United States Patent [19]
Jentsch et al.

[11] Patent Number: 6,127,158
[45] Date of Patent: Oct. 3, 2000

[54] UBIQUITIN CONJUGATING ENZYMES

[75] Inventors: Stefan Jentsch, Heidelberg, Germany; Marc W. Kirschner, Newton, Mass.; Randall W. King, Brookline, Mass.; P. Renee Yew, Brookline, Mass.

[73] Assignee: President and Fellows of Harvard College, Cambridge, Mass.

[21] Appl. No.: 08/350,468

[22] Filed: Dec. 7, 1994

[51] Int. Cl.[7] .............................. C12N 9/10; C12N 15/54
[52] U.S. Cl. .................. 435/193; 435/320.1; 435/252.3; 536/23.2
[58] Field of Search ................................ 435/69.1, 252.3, 435/6, 320.1, 193; 536/23.2, 24.31, 24.33

[56] References Cited

U.S. PATENT DOCUMENTS 5,798,245   8/1998   Anderson et al. ...................... 435/194

OTHER PUBLICATIONS

Suggs et al., PNAS, 1981, vol. 78, pp. 6613–6617.
George et al, "Current methods in sequence comparison and analysis," in Macromolecular Sequencing and Synthesis, Selected Methods and Applications, 1988, D.H. Schlesinger (ed.), Alan R. Liss, Inc., New York, NY, pp. 127–149.
Barton, "Protein sequence alignment and database scanning," in Protein Structure Prediction, A Practical Approach, 1996 IRL Press at Oxford University Press, Oxford, UK, pp. 31–63).
Jentsch, S., *A. Rev. Genet. 26*: 177 (1992).
Hershko, A. & Ciechanover, A., *A. Rev. Biochem. 61*: 761 (1992).
Method in Enzymology, vol. 155, pp. 468–482 (1987) Carle and Olson, "Orthogonal–Field–Alternation Gel Electrophoresis".
Schneider et al, EMBO J 9:1431–1435 (1990) "The Human Ubiquitin Carrier Protein E2 (MR=17000) is Homologous . . . ".
Maundrell et al, EMBO J 7:2203–2209 (1988) "Sequence Analysis of ARS Elements in Fission Yeast".
Silver et al., EMBO J 11:3091–3098 (1992) "A Chimeric Ubiquitin Conjugating Enzyme that Combines . . . ".
Rigby et al, J Mol Biol 113:237–251 (1977) "Labeling Deoxyribonucleic Acid to High Specific Activity . . . ".
Tabor & Richardson, PNAS 82:1074–1078 (1985) "A Bacteriophage T7 RNA Polymerase/Promoter System . . . ".
Gould et al., PNAS 86:1934–1938 (1989) "Use of the DNA Polymerase Chain Reaction for Homology . . . ".
Anderson et al. (1995). N–Geneseq Entry Q86859.

*Primary Examiner*—Robert A. Wax
*Assistant Examiner*—Bradley S. Mayhew
*Attorney, Agent, or Firm*—Kevin M. Farrell

[57] ABSTRACT

Disclosed herein are novel ubiquitin-conjugating enzymes and methods for using same. More specifically, disclosed are nucleic acid sequences encoding the UBC9 protease.

8 Claims, 2 Drawing Sheets

*Figure 1*

```
sUBC9  Met Ser Ser Leu Cys Leu Gln Arg Leu Gln Glu Arg Lys Lys Trp Arg Lys Asp His Pro Phe Gly Phe
xUBC9  Met Ser Gly Ile Ala Leu Ser Arg Leu Ala Gln Glu Arg Lys Ala Trp Arg Lys Asp His Pro Gly Phe
hUBC9                                      Gln Glu Arg Lys Ala Trp Arg Lys Asp His Pro Gly Phe sUBC9  Tyr Ala Lys Pro Val Lys Lys Ala Asp Gly Ser Met Asp Leu Gln Lys Trp Glu Ala Gly Ile Pro Gly Lys
xUBC9  Val Ala Val Pro Thr Lys Asn Pro Asp Gly Thr Met Asn Leu Met Asn Trp Glu Cys Ala Ile Pro Gly Lys
hUBC9  Val Ala Val Pro Thr Lys Asn Pro Asp Gly Thr Met Asn Leu Met Asn Trp Glu Cys Ala Ile Pro Gly Lys sUBC9  Glu Gly Thr Asn Trp Ala Gly Gly Val Tyr Pro Ile Thr Val Glu Tyr Pro Asn Glu Tyr Pro Ser Lys Pro
xUBC9  Lys Gly Thr Pro Trp Glu Gly Gly Leu Phe Lys Leu Arg Met Leu Phe Lys Asp Asp Tyr Pro Ser Ser Pro
hUBC9  Lys Gly Thr Pro Trp Glu Gly Gly Leu Phe Lys Leu Arg Met Leu Phe Lys Asp Asp Tyr Pro Ser Ser Pro sUBC9  Pro Lys Val Lys Phe Pro Ala Gly Phe Tyr His Pro Asn Val Tyr Pro Ser Gly Thr Ile Cys Leu Ser Ile
xUBC9  Pro Lys Cys Lys Phe Glu Pro Pro Leu Phe His Pro Asn Val Tyr Pro Ser Gly Thr Val Cys Leu Ser Ile
hUBC9  Pro Lys Cys Lys Phe Glu Pro Pro Leu Phe His Pro Asn Val Tyr Pro Ser Gly Ala Val Cys Leu Ser Ile sUBC9  Leu Asn Glu Asp Gln Asp Trp Arg Pro Ala Ile Thr Leu Lys Gln Ile Val Leu Gly Val Gln Asp Leu Leu
xUBC9  Leu Glu Glu Asp Lys Asp Trp Arg Pro Ala Ile Thr Ile Lys Gln Ile Leu Leu Gly Ile Gln Glu Leu Leu
hUBC9  Leu Glu Glu Asp Lys Asp Trp Arg Pro Ala Ile Thr Ile Lys Gln Ile Leu Leu Gly Ile Gln Glu Leu Leu sUBC9  Asp Ser Pro Asn Pro Asn Ser Pro Ala Gln Glu Pro Ala Trp Arg Ser Phe Ser Arg Asn Lys Ala Glu Tyr
xUBC9  Asn Glu Pro Asn Ile Gln Asp Pro Ala Gln Ala Glu Ala Tyr Thr Ile Tyr Cys Gln Asn Arg Val Glu Tyr
hUBC9  Asn Glu Pro Asn Ile Gln Asp Pro Ala Gln Ala Glu Ala Tyr Thr Ile Tyr Cys Gln Asn Arg Val Asp Tyr sUBC9  Asp Lys Lys Val Leu Leu Gln Ala Lys Gln Tyr Ser Lys
xUBC9  Glu Lys Arg Val Arg Ala Gln Ala Lys Lys Phe Ala Pro Ser
hUBC9  Glu Thr Ser Ala Pro Lys Pro Lys Pro Arg Ser
```

Figure 2

```
TCTAGAGCACTAATCAGTTTATTAAAATCTTCTGTCTTCACATTATTCTCGTTACCGTTA
TTTTTCATCAAATTTGCGAACTCATTTTGCAAATCTACCATCATTTCTTTCAATTCTGGG
TCCTCTTCAGATTCATTAGCTACCTGTACGCCATCACTGTCCTTACTTTCGGCATTCTTC
TCTTTGTTTTCACTATCGTTGTACACAGAACCCTTCGCTTGCACATCATCGGGCTCTGCT
TCATCCAGTTTAGTGGGATCTTCATCTAAAGGTCATCCAAATCATCAAAATTATCGTAC
TCGTTTTCATTCATTACTTCGTGTTGTATGTTTGGCATTTCTTCTTTCCGTCAATACTTC
GGTTCCCACAATTTGTAATTCTTTCTTCACTTTATATCTCTCAGAAACCGCGTTTAACAT
CTGGAAATTAAAAATTATTCCTGTCTCCATAACAAACATTTAAAAAAGAAGAGAAATTT

AGCATAGGATAAGCACACACTGGCACCATTTTTTGGAAGCAATATGAGTAGTTTGTGTCT
                                         MetSerSerLeuCysLe

ACAGCGTCTTCAGGAAGAAAGGTAAGTAGTAGTTTTCCTCCTTTTATGCTTACATTCTGT
uGlnArgLeuGlnGluGluAr

AGGCATACACAATTTCATCCAGCGGTATACTAACAAATCGATGAACTTAACTTGTTTTAC

TTGAATAACAGAAAAAAATGGAGAAGGATCATCCATTTGGATTTTATGCCAAACCAGTT
        gLysLysTrpArgLysAspHisProPheGlyPheTyrAlaLysProVal

AAGAAAGCTGATGGGTCCATGGATTTACAGAAATGGGAAGCTGGTATCCCAGGCAAAGAA
LysLysAlaAspGlySerMetAspLeuGlnLysTrpGluAlaGlyIleProGlyLysGlu

GGTACAAACTGGGCGGGTGGTGTGTACCCAATTACAGTCGAATATCCAAATGAATATCCT
GlyThrAsnTrpAlaGlyGlyValTyrProIleThrValGluTyrProAsnGluTyr*Pro*

TCAAAACCTCCAAAGGTTAAATTTCCAGCCGGATTTTATCATCCAAACGTGTATCCAAGT
SerLysProProLysValLysPheProAlaGlyPheTyrHisProAsnValTyrProSer

GGCACAATATGTTTAAGTATTTTAAATGAAGATCAAGATTGGAGACCCGCCATCACGTTA
GlyThrIle*Cys*LeuSerIleLeuAsnGluAspGlnAspTrpArgProAlaIleThrLeu

AAACAAATTGTTCTTGGGGTTCAGGATCTTTTAGACTCTCCAAATCCAAATTCCCCTGCT
LysGlnIleValLeuGlyValGlnAspLeuLeuAspSerProAsnProAsnSerProAla

CAAGAGCCTGCATGGAGATCATTTTCAAGAAATAAGGCGGAATATGACAAGAAAGTTTTG
GlnGluProAlaTrpArgSerPheSerArgAsnLysAlaGluTyrAspLysLysValLeu

CTTCAAGCTAAACAGTACTCTAAATAGAGGGAATCCATCTTTCCCATTCTTCCTCCTTTT
LeuGlnAlaLysGlnTyrSerLys

GTACTTTATTTAACTAATGTCGTTGTGTAACAAAAATAGAGCAAAATAACATTATTTACA
AATTCTCAAAAATAATTTTTTGCTCTTTGTTTCTTATGCTAAGTAAATAGAAAGATATTT
TTTGTACCATTTTCTATAAGTATGGCAACTATATACACTTTAATAAATCTATTGGTTAGT
AGAATTTTCATTCATTTTGTAGTGAATGAAACTAGCCAACGTAGTAAAGCAATCATGGCA
TCTTTCTTTTAGTTCGGGATTTTTGTTTTTATCAACCATTTTGAATTGCTGCCTCAAATT
TGGTACAACTTGGTCTTTTAGAATAGATAAAAATCCACCCCTTACAAATATT
```

UBIQUITIN CONJUGATING ENZYMES

FUNDING

Work described herein was supported by funding from the National Institutes of Health. The United States Government has certain rights in the invention.

BACKGROUND OF THE INVENTION

The ubiquitin-mediated proteolysis system is the major pathway for the selective, controlled degradation of intracellular proteins in eukaryotic cells. Ubiquitin modification of a variety of protein targets within the cell appears to be important in a number of basic cellular functions such as regulation of gene expression, regulation of the cell-cycle, modification of cell surface receptors, biogenesis of ribosomes, and DNA repair. One major function of the ubiquitin-mediated system is to control the half-lives of cellular proteins. The half-life of different proteins can range from a few minutes to several days, and can vary considerably depending on the cell-type, nutritional and environmental conditions, as well as the stage of the cell-cycle.

Targeted proteins undergoing selective degradation, presumably through the actions of a ubiquitin-dependent proteosome, are covalently tagged with ubiquitin through the formation of an isopeptide bond between the C-terminal glycyl residue of ubiquitin and a specific lysyl residue in the substrate protein. This process is catalyzed by a ubiquitin-activating enzyme (E1) and a ubiquitin-conjugating enzyme (E2), and in some instances may also require auxiliary substrate recognition proteins (E3s). Following the linkage of the first ubiquitin chain, additional molecules of ubiquitin may be attached to lysine side chains of the previously conjugated moiety to form branched multi-ubiquitin chains.

The conjugation of ubiquitin to protein substrates is a multi-step process. In an initial ATP requirng step, a thiolester is formed between the C-terminus of ubiquitin and an internal cysteine residue of an E1 enzyme. Activated ubiquitin is then transferred to a specific cysteine on one of several E2 enzymes. Finally, these E2 enzymes donate ubiquitin to protein substrates. Substrates are recognized either directly by ubiquitin-conjugated enzymes or by associated substrate recognition proteins, the E3 proteins, also known as ubiquitin ligases.

Ubiquitin is itself a substrate for ubiquitination. Depending on the ubiquitin-conjugating enzyme and the nature of the substrate, specific lysine residues of ubiquitin are used as acceptor sites for further ubiquitinations. This can lead to either a linear multi-ubiquitin chain or multi-ubiquitin "trees". Although the attachment of a single ubiquitin moiety to a substrate can be sufficient for degradation, multi-ubiquitination appears to be required in most cases.

Many proteins that control cell-cycle progression are short-lived. For example, regulation of oncoproteins and anti-oncoproteins clearly plays an important role in determining steady-state levels of protein expression, and alterations in protein degradation are as likely as changes in transcription and/or translation to cause either the proliferative arrest of cells, or alternatively, the transformation of cells.

SUMMARY OF THE INVENTION

The present invention relates to the discovery in eukaryotic cells, particularly human cells and certain yeast cells, of a novel ubiquitin conjugating enzyme (hereinafter "UBC9"). In human cells, the enzyme likely functions to mediate ubiquitination of cell-cycle regulatory proteins, such as p53 and/or cyclin, and possibly transcriptional regulatory proteins such as myc and fos, and is therefore presumably involved in regulating cell-cycle progression, e.g. cell growth.

One aspect of the invention features a substantially pure preparation of a human UBC9 polypeptide ("hUBC9"), or a fragment thereof, which can function as a ubiquitin conjugating enzyme. In a preferred embodiment: the polypeptide has an amino acid sequence at least 90% homologous to the amino acid sequence of SEQ ID No: 2; the polypeptide has an amino acid sequence at least 95% homologous to the amino acid sequence of SEQ ID No: 2; the polypeptide has an amino acid sequence at least 97% homologous to the amino acid sequence of SEQ ID No: 2; the polypeptide has an amino acid sequence identical to the amino acid sequence of SEQ ID No: 2. In a preferred embodiment: the fragment comprises at least 5 contiguous amino acid residues of SEQ ID No: 2; the fragment comprises at least 20 contiguous amino acid residues of SEQ ID No: 2; the fragment comprises at least 50 contiguous amino acid residues of SEQ ID No: 2.

Another aspect of the invention features a substantially pure preparation of a Xenopus UBC9 polypeptide ("xUBC9"), or a fragment thereof, which can function as a ubiquitin conjugating enzyme. In a preferred embodiment: the polypeptide has an amino acid sequence at least 90% homologous to the amino acid sequence of SEQ ID No: 4; the polypeptide has an amino acid sequence at least 95% homologous to the amino acid sequence of SEQ ID No: 4; the polypeptide has an amino acid sequence at least 97% homologous to the amino acid sequence of SEQ ID No: 4; the polypeptide has an amino acid sequence identical to the amino acid sequence of SEQ ID No: 4. In a preferred embodiment: the fragment comprises at least 5 contiguous amino acid residues of SEQ ID No: 4; the fragment comprises at least 20 contiguous amino acid residues of SEQ ID No: 4; the fragment comprises at least 50 contiguous amino acid residues of SEQ ID No: 4.

Another aspect of the invention features a substantially pure preparation of a Saccharomyces UBC9 polypeptide ("sUBC9"), or a fragment thereof, which can function as a ubiquitin conjugating enzyme. In a preferred embodiment: the polypeptide has an amino acid sequence at least 90% homologous to the amino acid sequence of SEQ ID No: 6; the polypeptide has an amino acid sequence at least 95% homologous to the amino acid sequence of SEQ ID No: 6; the polypeptide has an amino acid sequence at least 97% homologous to the amino acid sequence of SEQ ID No: 6; the polypeptide has an amino acid sequence identical to the amino acid sequence of SEQ ID No: 6. In a preferred embodiment: the fragment comprises at least 5 contiguous amino acid residues of SEQ ID No: 6; the fragment comprises at least 20 contiguous amino acid residues of SEQ ID No: 6; the fragment comprises at least 50 contiguous amino acid residues of SEQ ID No: 6.

Another aspect of the present invention features an hUBC9 polypeptide which functions in one of either role of an agonist of cell-cycle regulation or an antagonist of cell-cycle regulation. In a preferred embodiment the hUBC9 polypeptide has: an ability to mediate ubiquitination of cellular proteins, e.g. cell-cycle regulatory proteins, such p53 and/or cyclin, or transcriptional regulatory proteins such as myc or fos; an ability to mediate ubiquitin-dependent degradation of cellular proteins, e.g. cell-cycle regulatory proteins, or transcriptional regulatory proteins; an ability to affect the cellular half-life of a cell-cycle regulatory protein or transcriptional regulatory proteins, e.g. in normal proliferating cells, virally-infected cells (e.g. in papillomavirus infected cells) or transformed cells. The biological activity can further include the ability to bind and conjugate ubiquitin, as well as bind and transfer ubiquitin to a ubiquitin ligase (E3) enzyme.

Yet another aspect of the present invention concerns an immunogen comprising a UBC9 polypeptide, or a fragment thereof, in an immunogenic preparation, the immunogen being capable of eliciting an immune response specific for the UBC9 polypeptide; e.g. a humoral response, e.g. an antibody response; e.g. a cellular response.

A still further aspect of the present invention features an antibody preparation specifically reactive with an epitope of the UBC9 immunogen, e.g. reactive with hUBC9, e.g. reactive with xUBC9, e.g. reactive with sUBC9.

Another aspect of the present invention features recombinant hUBC9 polypeptides, or a fragment thereof, having an amino acid sequence preferably: at least 90% homologous to SEQ ID No: 2; at least 95% homologous to SEQ ID No: 2; at least 97% homologous to SEQ ID No: 2. The recombinant hUBC9 protein can consist essentially of an amino acid sequence homologous to SEQ ID NO: 2, or can comprise that amino acid fused to other unrelated polypeptide sequences to form a chimeric protein. In preferred embodiments: the hUBC9 polypeptide mediates ubiquitination of cellular proteins, e.g. cell-cycle regulatory proteins, or transcriptional regulatory proteins, and can bring about ubiquitin-dependent degradation of these cellular proteins. Recombinant hUBC9 homologs which antagonize the ubiquitin conjugating activity of the wild-type form of the enzyme are also contemplated, such as dominant negative mutants.

Likewise the present invention also features recombinant xUBC9 polypeptides having an amino acid sequence preferably: at least 90% homologous to SEQ ID No: 4; at least 95% homologous to SEQ ID No: 4; at least 97% homologous to SEQ ID No: 4. In a preferred embodiment, the recombinant xUBC9 protein functions in one of either role of an agonist of cell cycle regulation or an antagonist of cell cycle regulation, such as by mediating ubiquitination of cellular proteins involved in cell-cycle and transcriptional regulation.

Yet another aspect of the present invention features recombinant sUBC9 polypeptides, or a fragment thereof, having an amino acid sequence preferably: at least 90% homologous to SEQ ID No: 6; at least 95% homologous to SEQ ID No: 6; at least 97% homologous to SEQ ID No: 6. In a preferred embodiment, the recombinant sUBC9 protein functions in one of either role of an agonist of cell-cycle regulation or an antagonist of cell-cycle regulation, as, for example by facilitating ubiquitination of cellular proteins of Saccharomyces cells.

In yet other preferred embodiments, the recombinant xUBC9 and sUBC9 are fusion proteins further comprising a second polypeptide portion having an amino acid sequence from a protein unrelated to the protein of SEQ ID No: 4 or 6. Such fusion proteins, like the hUBC9 fusion proteins, can be functional in a two-hybrid assay, or facilitate matrix-binding characteristics.

Another aspect of the present invention provides a substantially pure nucleic acid having a nucleotide sequence which encodes an hUBC9 polypeptide, or a fragment thereof, having an amino acid sequence at least 90% homologous to SEQ ID NO: 2. In a more preferred embodiment, the nucleic acid encodes a protein having an amino acid sequence at least 95% homologous to SEQ ID No: 2; and more preferably at least 97% homologous to SEQ ID No: 2. The nucleic acid preferably encodes: an hUBC9 polypeptide which mediates ubiquitination of cellular proteins, e.g. cell-cycle regulatory proteins, such as p53 or cyclins, or transcriptional regulatory proteins such as myc or fos; an hUBC9 polypeptide which mediates ubiquitin-dependent degradation of cellular and/or viral proteins, e.g. cell-cycle or transcriptional regulatory proteins, an hUBC9 polypeptide which affects the cellular half-life of a cell-cycle or transcriptional regulatory protein.

The nucleic acid can be a chimeric gene, comprising, in addition to the hUBC9 coding sequence, coding sequences for one or more additional polypeptides (e.g. encoding an hUBC9 fusion protein), as well as transcriptional and translational regulatory sequences not normally associated with an hUBC9 gene.

Another aspect of the present invention provides a substantially pure nucleic acid having a nucleotide sequence which encodes an xUBC9 polypeptide, or a fragment thereof, having an amino acid sequence at least 90% homologous to SEQ ID NO: 4. In a more preferred embodiment, the nucleic acid encodes a protein having an amino acid sequence at least 95% homologous to SEQ ID No: 4; and more preferably at least 97% homologous to SEQ ID No: 4.

Another aspect of the present invention provides a substantially pure nucleic acid having a nucleotide sequence which encodes an sUBC9 polypeptide, or a fragment thereof, having an amino acid sequence at least 90% homologous to SEQ ID NO: 4. In a more preferred embodiment, the nucleic acid encodes a protein having an amino acid sequence at least 95% homologous to SEQ ID No: 4; and more preferably at least 97% homologous to SEQ ID No: 4.

In yet a further preferred embodiment, the nucleic acid which encodes a UBC9 polypeptide of the present invention, or a fragment thereof, hybridizes under stringent conditions to a nucleic acid probe corresponding to at least 12 consecutive nucleotides of one of SEQ ID Nos: 1, 3 or 5; more preferably to at least 20 consecutive nucleotides of said sequences; more preferably to at least 40, 50, 75 or 100 consecutive nucleotides.

Furthermore, in certain preferred embodiments, UBC9 encoding nucleic acid will comprise a transcriptional regulatory sequence, e.g. at least one of a transcriptional promoter or transcriptional enhancer sequence, operably linked to the UBC9 gene sequence so as to render the UBC9 gene sequence suitable for use as an expression vector. In one embodiment, the UBC9 gene is provided as a sense construct. In another embodiment, the UBC9 gene is provided as an anti-sense construct, providing, upon transcription, a mRNA which is complementary to mRNA which can be translated to produce a UBC9.

The present invention also features transgenic non-human animals, which either express a heterologous UBC9 gene or which mis-express an endogenous UBC9 gene, e.g. expression of the hUBC9 gene is disrupted. Such a transgenic animal can serve as an animal model for studying cellular disorders comprising mutated or mis-expressed UBC9 alleles.

The present invention also provides a probe/primer comprising a substantially purified oligonucleotide, wherein the oligonucleotide comprises a region of nucleotide sequence which hybridizes under stringent conditions to at least 10, more preferably at least 20, 30, 50, or 75 consecutive nucleotides of sense or antisense sequence of SEQ ID No: 1 or naturally occurring mutants thereof In preferred embodiments, the probe/primer further comprises a label group attached thereto and able to be detected, e.g. the label group is selected from a group consisting of radioisotopes, fluorescent compounds, enzymes, and enzyme co-factors. Such probes can be used as a part of a diagnostic test kit for identifying transformed cells, such as for measuring a level of an hUBC9 nucleic acid in a sample of cells isolated from a patient; e.g. measuring the UBC9 mRNA level in a cell; e.g. determining whether the genomic UBC9 gene has been mutated or deleted.

Yet another aspect of the present invention relates to a method for identifying an inhibitor of UBC9-mediated ubiquitination by (i) providing a ubiquitin-conjugating system including UBC9, a UBC9 ubiquitination substrate protein, and ubiquitin under conditions which promote the ubiquitination of the substrate protein, and (ii) measuring the level of ubiquitination of the substrate protein brought about by the system in the presence and absence of a candidate agent. A decrease in the level of ubiquitin conjugation is indicative of an inhibitory activity for the candidate agent. The level of ubiquitination of the regulatory protein can be measured by determining the actual concentration of protein:ubiquitin conjugates formed; or inferred by detecting some other quality of the subject protein affected by ubiquitination, including the proteolytic degradation of the protein.

The present invention also provides a method for treating an animal having unwanted cell growth characterized by abherent expression of a ubiquitin-sensitive cellular protein, such as a loss of wild-type p53 function or over expression of a cyclin or myc protein, comprising administering a therapeutically effective amount of an agent able to inhibit a ubiquitin conjugating activity of the subject hUBC9 protein where it is desirable to increase the amount of the regulatory protein; or administering an agent which potentiates the UBC9-dependent ubiquitination of the regulatory protein in those circumstances where it is desirable to decrease the cellular concentration of the protein.

The present invention also provides a method for treating an animal having an unwanted mycotic infection, comprising administering a therapeutically effective amount of an agent able to inhibit a ubiquitin conjugating activity of a fungal UBC9 enzyme, such as the subject sUBC9 protein, without substantially inhibiting the UBC9 activity.

Another aspect of the present invention provides a method of determining if a subject, e.g. a human patient, is at risk for a disorder characterized by unwanted cell proliferation, comprising detecting, in a tissue of the subject, the presence or absence of a genetic lesion characterized by at least one of (i) a mutation of a gene encoding a protein represented by SEQ ID No: 2, or a homolog thereof; or (ii) the misexpression of the hUBC9 gene. In preferred embodiments: detecting the genetic lesion comprises ascertaining the existence of at least one of a deletion of one or more nucleotides from the gene, an addition of one or more nucleotides to the gene, a substitution of one or more nucleotides of the gene, a gross chromosomal rearrangement of the gene, a gross alteration in the level of a messenger RNA transcript of the gene, the presence of a non-wild type splicing pattern of a messenger RNA transcript of the gene, or a non-wild type level of the protein. For example, detecting the genetic lesion can comprise (i) providing a probe/primer comprising an oligonucleotide containing a region of nucleotide sequence which hybridizes to a sense or antisense sequence of SEQ ID No: 1 or naturally occurring mutants thereof or 5' or 3' flanking sequences naturally associated with the gene; (ii) exposing the probe/primer to nucleic acid of the tissue; and (iii) detecting, by hybridization of the probe/ primer to the nucleic acid, the presence or absence of the genetic lesion; e.g. wherein detecting the lesion comprises utilizing the probe/primer to determine the nucleotide sequence of the hUBC9 gene and, optionally, of the flanking nucleic acid sequences; e.g. wherein detecting the lesion comprises utilizing the probe/primer in a polymerase chain reaction (PCR); e.g. wherein detecting the lesion comprises utilizing the probe/primer in a ligation chain reaction (LCR). In alternate embodiments, the level of the protein is detected in an immunoassay.

Other features and advantages of the invention will be apparent from the following detailed description, and from the claims.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press:1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

BRIEF DESCRIPTION OF THE FIGURES

FIG. 1 is a sequence alignment of hUBC9 (human UBC9, SEQ ID No. 2), sUBC9 (yeast UBC9, SEQ ID No. 6) and xUBC9 (amphibia UBC9, SEQ ID No. 4).

FIG. 2 illustrates the primary structure of sUBC9 from the nucleotide and predicted amino acid sequence of the *S. cerevisiae* UBC9 gene (SEQ ID No. 7 for genomic sequence, SEQ ID No. 6 for amino acid sequence). The position of the intron was established by comparing genomic and cDNA sequences. Splice sites and putative branch point are underlined. Nucleotide numbers starting at the first nucleotide of the coding region are given on the left. The cysteine residue required for UBC9-ubiquitin thiolester formation, and the proline residue changed to serine in UBC9-1 are each shown in bold italics.

DETAILED DESCRIPTION OF THE INVENTION

The ubiquitin system is essential for a wide spectrum of cellular phenomena, and is a component of many biological regulatory mechanisms, including aspects of growth control, metabolic regulation, embryonic development, and cell-cycle progression.

The present invention is directed to the discovery of a family of related ubiquitin-conjugating enzymes ("UBC9"). In particular, members of this family have been cloned from various eukaryotic sources, and include, for example, a human ubiquitin-conjugating enzyme ("hUBC9"), a Xenopus ubiquitin-conjugating enzyme ("xUBC9"), and a Saccharomyces ubiquitin-conjugating enzyme ("sUBC9"). The nucleotide sequences for the human UBC9, the Xenopus UBC9, and the Saccharomyces UBC9 coding sequences are provided in SEQ ID Nos: 1, 3 and 5, respectively. The corresponding amino acid sequences are represented in SEQ ID Nos: 2, 4 and 6. The genomic sequence for the yeast UBC9 is presented in SEQ ID No: 7.

The biological activity of the UBC9 proteins of the present invention is likely to be important in a number of basic cellular functions, such as regulation of gene expression, regulation of the cell-cycle, modification of cell surface receptors, biogenesis of ribosomes, and DNA repair. In particular, one expected function of members of this family of enzymes in ubiquitin-mediated systems is to control the cellular half-lives of various proteins. For instance, hUBC9 is likely to be implicated in the ubiquitin-mediated inactivation of cell-cycle and transcriptional regulatory proteins, such as p53, myc, cyclins, fos, MATα2, or the adenovirus E1A protein. Consequently, the present invention identifies a potential molecular target, e.g., UBC9, for altering the cellular half-life of cell cycle regulatory proteins and thereby modulating, for example, cell proliferation, apoptosis, and cellular sensitivity to chemotherapeutics and DNA damaging agents.

Accordingly, the present invention makes available diagnostic and therapeutic assays, reagents and kits for detecting and treating proliferative disorders arising from, for example, tumorogenic transformation of cells, or other hyperplastic or neoplastic transformation processes. For example, the present invention makes available reagents, such as antibodies and nucleic acid probes, for detecting altered complex formation, and/or altered levels of hUBC9 expression, and/or hUBC9-gene deletion or mutation, in order to identify transformed cells. Moreover, the present invention provides a method of treating a wide variety of pathological cell proliferative conditions, such as by gene therapy utilizing recombinant gene constructs encoding the subject hUBC9 proteins, by providing peptidomimetics which either inhibit or potentiate the interaction between hUBC9 and a substrate protein, or by providing inhibitors of the catalytic activity of hUBC9. Such methods can also be used in tissue culture, such as to regulate the transformation of cells in vitro.

In similar fashion, the present invention also makes available diagnostic and therapeutic assays for detecting and treating yeast/fungal infections, where such infections occur in an animal, e.g. humans, or on a non-living object, such as food or medical instruments. For example, given the probable role of the subject UBC9s, namely sUBC9, in regulation of proteins involved in growth, mating and proliferation of yeast, inhibitors of the subject ubiquitin conjugating enzyme can be used to treat mycotic infections, as disinfectants, or as food preservatives.

For convenience, certain terms employed in the specification, examples, and appended claims are collected here.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the terms "gene", "recombinant gene" and "gene construct" refer to a nucleic acid comprising an open reading frame encoding a UBC9 polypeptide of the present invention, including both exon and (optionally) intron sequences. In preferred embodiments, the nucleic acid is DNA or RNA. Exemplary recombinant genes include nucleic acids which encode all or a catalytically active portion of the hUBC9 protein represented in SEQ ID No: 2, the xUBC9 protein represented in SEQ ID No: 4, or the sUBC9 protein represented in SEQ ID No: 6. The term "intron" refers to a DNA sequence present in a given UBC9-gene which is not translated into protein and is generally found between exons.

The term "transfection" refers to the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous nucleic acid, and, for example, the transformed cell expresses a recombinant form of one of the subject UBC9 proteins.

"Cells" or "cell cultures" or "recombinant host cells" or "host cells" are often used interchangeably as will be clear from the context. These terms include the immediate subject cell which expresses a ubiquitin-conjugating enzyme of the present invention, and, of course, the progeny thereof. It is understood that not all progeny are exactly identical to the parental cell, due to chance mutations or difference in environment. However, such altered progeny are included in these terms, so long as the progeny retain the characteristics relevant to those conferred on the originally transformed cell. In the present case, such a characteristic might be the ability to produce a recombinant UBC9-protein.

As used herein, the term "vector" refers to a nucleic acid molecule capable of transporting another nucleic acid to which it has been linked. The term "expression vector" includes plasmids, cosmids or phages capable of synthesizing the subject proteins encoded by their respective recombinant genes carried by the vector. Preferred vectors are those capable of autonomous replication and/expression of nucleic acids to which they are linked. In the present specification, "plasmid" and "vector" are used interchangeably as the plasmid is the most commonly used form of vector. Moreover, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, as well as polyadenylation sites, which induce or control transcription of protein coding sequences with which they are operably linked. In preferred embodiments, transcription of a recombinant UBC9-gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the regulatory protein.

The term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of an epithelial lineage, e.g. cervical squamous cells. In an illustrative embodiment of epithelial-specific promoters, gene constructs can be used as a part of gene therapy to deliver, for example, genes encoding a domaint negative hUBC9 mutant, in order to inhibit degradation of p53 required for the pathogenesis of certain papillomavirus-mediated disorders, e.g. papillomas, or to direct expression of an antisense construct of the subject ubiquitin-conjugating enzyme in only epithelial tissue. The term also covers so-called "leaky" promoters, which regulate expression of a selected DNA primarily in one tissue, but cause expression in other tissues as well.

As used herein, a "transgenic animal" is any animal, preferably a non-human mammal in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of the subject UBC9 protein, e.g. either agonistic or antagonistic forms, or in which the endogenous UBC9 gene has been disrupted. However, transgenic animals in which the recombinant UBC9 gene is silent are also contemplated, as for example, the FLP or CRE recombinase dependent constructs described below. The "non-human animals" of the invention include vertebrates such as rodents, non-human primates, sheep, dog, cow, birds, amphibians, reptiles, etc. Preferred non-human animals are selected from the rodent family including rat and mouse, most preferably mouse. The term "chimeric animal" is used herein to refer to animals in which the recombinant gene is found, or in which the recombinant is expressed in some but not all cells of the animal. The term "tissue-specific chimeric animal" indicates that the recombinant UBC9 gene is present and/or expressed in some tissues but not others.

As used herein, the term "transgene" means a nucleic acid sequence (encoding, e.g., a UBC9 polypeptide), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

The term "evolutionarily related to", with respect to nucleic acid sequences encoding the subject ubiquitin-conjugating enzymes, refers to nucleic acid sequences which have arisen naturally in an organism, including naturally occurring mutants. The term also refers to nucleic acid sequences which, while derived from a naturally occurring enzyme, have been altered by mutagenesis, as for example, combinatorial mutagenesis described below, yet still encode polypeptides which have at least one activity of a UBC9 protein.

As described below, one aspect of this invention pertains to an isolated nucleic acid comprising a nucleotide sequence encoding one of the subject UBC9 proteins, fragments thereof encoding polypeptides having at least one biological activity of a UBC9 protein, and/or equivalents of such nucleic acids. The term "nucleic acid" as used herein is intended to include such fragments and equivalents. The term "equivalent" is understood to include nucleotide sequences encoding functionally equivalent UBC9 proteins or functionally equivalent peptides having an activity of a ubiquitin-conjugating enzyme such as described herein. Equivalent nucleotide sequences will include sequences that differ by one or more nucleotide substitutions, additions or deletions, such as allelic variants; and will also include sequences that differ from the nucleotide sequence of the hUBC9 cDNA represented in SEQ ID No: 1, the xUBC9 cDNA represented in SEQ ID No: 3, the sUBC9 cDNA represented in SEQ ID No: 5, or the sUBC9 genomic DNA represented in SEQ ID No: 7, due to the degeneracy of the genetic code. Equivalents will also include nucleotide sequences which hybridize under stringent conditions (i.e., equivalent to about 20–27° C. below the melting temperature ($T_m$) of the DNA duplex formed in about 1M salt) to the nucleotide sequence represented in at least one of SEQ ID Nos: 1, 3, 5 or 7. In one embodiment, equivalents will further include nucleic acid sequences derived from and evolutionarily related to the nucleotide sequences shown in any of SEQ ID Nos: 1, 3, 5 or 7.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding one of the subject UBC9 proteins preferably includes no more than 10 kilobases (kb) of nucleic acid sequence which naturally immediately flanks the UBC9 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

Polypeptides referred to herein as possessing the activity of a ubiquitin-conjugating enzyme (UBC9), e.g. are UBC9 agonists, are understood to have an amino acid sequence identical to or homologous with the amino acid sequences shown in any on of SEQ ID Nos: 2, 4 or 6, and which are capable of forming a thiol ester adduct with the C-terminal carboxyl group of ubiquitin and transferring the ubiquitin to an $\epsilon$-amino group in an acceptor protein by formation of an isopeptide bond. The biological activity of the subject UBC9 proteins can include participation in degradative pathways for selective proteolysis of constitutively or conditionally short-lived proteins as well as abnormal proteins. For instance, a UBC9 polpeptide of the present invention can be characterized by an ability to mediate ubiquitination of cellular and/or viral proteins, e.g. cell-cycle regulatory proteins such as p53, myc, fos, cyclins, MATα2 and/or E1A. Such a feature will typically be marked by an ability of UBC9 to mediate ubiquitin-dependent degradation or inactivation of such regulatory proteins, in normal proliferating cells, in virally-infected cells, e.g. by papillomavirus or adenovirus, or in transformed cells, e.g. in cancerous cells. Antagonistic forms of the subject UBC9 proteins are defined as proteins that are homologous, but not identical, to the UBC9 proteins represented in SEQ ID Nos: 2, 4 or 6, or that are fragments of the wild-type proteins, which inhibit the transfer of ubiquitin by the naturally occurring form of the ubiquitin-conjugating enzyme. For instance, mutations in the active site of the enzyme, e.g. Cys-93 (Cys-82 in SEQ ID No: 1), can produce dominant negative forms of the subject UBC9s which antagonize the action of the wild-type form of the protein.

Moreover, it will be generally appreciated that, under certain circumstances, it will be advantageous to provide homologs of naturally-occurring forms of the subject UBC9 proteins which are either agonists or antagonists, but of only a subset of that protein's biological activities. Thus, specific biological effects can be elicited by treatment with a homolog of limited function, and with fewer side effects relative to treatment with agonists or antagonists which are directed to all of the biological activities of that protein. For example, hUBC9 homologs can be generated which bind to and inhibit activation of other proteins in the ubiquitin pathway of one cell-cycle regulatory protein without substantially interfering with the ubiquitination of other cellular proteins by hUBC9.

Accordingly, one embodiment, the nucleic acid of the invention encodes a polypeptide which is either an agonist or antagonist of the human UBC9 protein and comprises an amino acid sequence identical or homologous to SEQ ID No: 2. Preferred nucleic acids encode a peptide having an hUBC9 protein activity, or which is an antagonist thereof, and being at least 90% homologous, more preferably 95% homologous and most preferably 97% homologous with an amino acid sequence shown in SEQ ID No: 2. Nucleic acids which encode agonist or antagonist forms of an hUBC9 protein and having at least about 98–99% homology with a sequence shown in SEQ ID No: 2 are also within the scope of the invention. Preferably, the nucleic acid is a cDNA molecule comprising at least a portion of the nucleotide sequence encoding an hUBC9 protein shown in SEQ ID No: 1. A preferred portion of the cDNA molecule shown in SEQ ID No: 1 includes the coding region of the molecule.

In another embodiment, the nucleic acid of the invention encodes a polypeptide which is either an agonist or antagonist of a Xenopus UBC9 protein, e.g. a *Xenopus laevis* UBC9, and comprises an amino acid sequence identical or homologous to SEQ ID No: 4. Preferred nucleic acids encode a peptide having an xUBC9 protein activity, or which is an antagonist thereof, and being at least 90% homologous, more preferably 95% homologous and most preferably 97% homologous with an amino acid sequence shown in SEQ ID No: 4. Nucleic acids which encode agonist or antagonist forms of an xUBC9 protein and having at least about 98–99% homology with a sequence shown in SEQ ID No: 4 are also within the scope of the invention. Preferably, the nucleic acid is a cDNA molecule comprising at least a portion of the nucleotide sequence encoding an xUBC9 protein shown in SEQ ID No: 3. A preferred portion of the cDNA molecule shown in SEQ ID No: 3 includes the coding region of the molecule. The present invention contemplates closely related homologs (orthologs) from other species of Xenopus, e.g. *Xenopus stellatoidea, Xenopus tropicalis, Xenopus parapsilosis, Xenopus krusei, Xenopus pseudotropicalis, Xenopus quillermondii*, or *Xenopus rugosa*.

In yet another embodiment, the nucleic acid of the invention encodes a polypeptide which is either an agonist or antagonist of a yeast UBC9 protein, e.g. a Saccharomyces UBC9, and comprises an amino acid sequence identical or homologous to SEQ ID No: 6. Preferred nucleic acids encode a polypeptide having an sUBC9 protein activity, or which is an antagonist thereof, and being at least 90% homologous, more preferably 95% homologous and most preferably 97% homologous with an amino acid sequence shown in SEQ ID No: 6. Nucleic acids which encode agonist or antagonist forms of an sUBC9 protein and having at least about 98–99% homology with a sequence shown in SEQ ID No: 6 are also within the scope of the invention. Preferably, the nucleic acid is a cDNA molecule comprising at least a portion of the nucleotide sequence encoding an sUBC9 protein shown in SEQ ID No: 5. A preferred portion of the cDNA molecule shown in SEQ ID No: 5 includes the coding region of the molecule.

Another aspect of the invention provides a nucleic acid which hybridizes under high or low stringency conditions to a nucleic acid which encodes a peptide having all or a portion of an amino acid sequence shown in one of SEQ ID Nos: 2, 4 or 6. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Isolated nucleic acids which differ in sequence from the nucleotide sequences represented in SEQ ID Nos: 1, 3 or 5 due to degeneracy in the genetic code are also within the scope of the invention. Such nucleic acids can encode functionally equivalent peptides (i.e., a polypeptide having a biological activity of a UBC9 protein) but differ in sequence from the sequence shown in SEQ ID No: 1, 3 or 5 due to degeneracy in the genetic code. For example, a number of amino acids are designated by more than one triplet. Codons that specify the same amino acid, or synonyms (for example, CAU and CAC are synonyms for histidine) may result in "silent" mutations which do not affect the amino acid sequence of the subject UBC9 protein. However, it is expected that DNA sequence polymorphisms that do lead to changes in the amino acid sequences of the present hUBC9 protein will exist from one human subject to the next. One skilled in the art will appreciate that these variations in one or more nucleotides (up to about 3–4% of the nucleotides) of the nucleic acids encoding peptides having an activity of, for example, an hUBC9 protein may exist among individuals due to natural allelic variation. Any and all such nucleotide variations and resulting amino acid polymorphisms are within the scope of this invention.

Fragments of the nucleic acid encoding an active portion of one of the subject ubiquitin-conjugating enzymes are also within the scope of the invention. As used herein, a fragment of the nucleic acid encoding an active portion of a UBC9 protein refers to a nucleotide sequence having fewer nucleotides than the nucleotide sequence encoding the entire amino acid sequence of the protein but which encodes a peptide which possess agonistic or antagonistic activity relative to a naturally occurring form of the enzyme.

Nucleic acid fragments within the scope of the invention also include those capable of hybridizing under high or low stringency conditions with nucleic acids from other species for use in screening protocols to detect UBC9 homologs. Comparison of the nucleic acid sequences of those portions of the protein of near identity between the yeast UBC9 and vertebrate UBC9 (see FIG. 1) reveal that oligonucleotide primers can be generated, which are only several fold degenerate, for detecting and isolating UBC9 clones in other eukaryotes. For example, the oligonucleotides
GSYATYCCAGGMAARRAAGGKAC and GAYTG-GAGRCCMGCMATCACRWTHAAA or the antisense forms thereof,
GTMCCTTYYTTKCC-TGGRATRSC and
TTTDAWYGTGATKGCKGGYCTCCARTC, can be used to detect UBC9 homologs in other vertebrate species, e.g. mice, rats, chickens, as well as other invertebrate species, including yeast and other fungus, as well as worms such as of phyla Annelida, Acanthocephala, Aschelminthes, and Platyhelminthes.

Nucleic acids within the scope of the invention may also contain linker sequences, modified restriction endonuclease sites and other sequences useful for molecular cloning, expression or purification of recombinant UBC9. For instance, the nucleic acid may include intronic sequences which can be excised from the transcript to provide a contiguous coding sequence. An illustrative intron-containing sequence is represented in SEQ ID No: 7, which includes an apparent intronic sequence in the genomic clone of sUBC9.

As indicated by the examples set out below, a nucleic acid encoding a peptide having an activity of the subject ubiquitin-conjugating enzymes may be obtained from mRNA or genomic DNA present in any of a number of eukaryotic cells in accordance with protocols described herein, as well as those generally known to those skilled in the art. A cDNA encoding a homolog of the human UBC9 protein, for example, can be obtained by isolating total mRNA from a cell, e.g. a mammalian cell. Double stranded CDNAs can then be prepared from the total MRNA, and subsequently inserted into a suitable plasmid or bacteriophage vector using any one of a number of known techniques. A gene encoding a UBC9 protein can also be cloned using established polymerase chain reaction techniques in accordance with the nucleotide sequence information provided by the invention.

Another aspect of the invention relates to the use of the isolated nucleic acid in "antisense" therapy. As used herein, "antisense" therapy refers to administration or in situ generation of oligonucleotide probes or their derivatives which specifically hybridizes (e.g. binds) under cellular conditions, with the cellular mRNA and/or genomic DNA encoding a UBC9 protein so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a UBC9-protein, e.g. the human UBC9 gene represented in SEQ ID No: 1. If placed under the control of a regulatable promoter, activation of the expression construct is lethal. Thus, in one aspect, the invention provides a means for killing a cell or population of cells. Alternatively, the antisense construct can be an oligonucleotide probe which is generated ex vivo and which, when introduced into the cell causes inhibition of expression by hybridizing with the mRNA and/or genomic sequences encoding one of the subject UBC9 proteins. Such oligonucleotide probes are preferably modified oligonucleotide which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der Krol et al. (1988) *Biotechniques* 6:958–976; and Stein et al. (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind. Such diagnostic tests are described in further detail below.

This invention also provides expression vectors containing a nucleic acid encoding the subject UBC9 proteins, operably linked to at least one transcriptional regulatory sequence. Operably linked is intended to mean that the nucleic acid is linked to a transcriptional regulatory sequence in a manner which allows expression of the enzyme encoded by the nucleic acid, and that expression is, for example, either constitutively or inducibly controlled by the transcriptional regulatory sequence. Regulatory sequences are art-recognized. Accordingly, the term regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences—sequences that control the expression of a DNA sequence when operatively linked to it may be used in these vectors to express DNA sequences encoding the UBC9 proteins of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast alpha-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered. In one embodiment, the expression vector includes a DNA encoding the subject hUBC9 protein, e.g. a recombinant hUBC9 protein, e.g. a recombinant protein having an agonistic activity relative to a naturally-occurring form of hUBC9, or alternatively, having an antagonistic activity relative to a naturally-occurring form of hUBC9. Similar expression vectors for producing recombinant forms of the xUBC9 and sUBC9 proteins are also contemplated. Such expression vectors can be used to transfect cells in order to produce proteins or peptides, including fusion proteins or peptides encoded by nucleic acids as described herein.

Moreover, UBC9-expression vectors can be used as a part of a gene therapy protocol to reconstitute UBC9 function in a cell in which UBC9 is misexpressed, or alternatively, to provide an antagonist of the naturally-occurring UBC9 or an antisense construct—such as to inhibit the UBC9-mediated degradation of a cell-cycle regulatory protein. For instance, expression constructs of the subject hUBC9-proteins may be administered in any biologically effective carrier, e.g. any formulation or composition capable of effectively transfecting cells in vivo with a recombinant hUBC9-gene. Approaches include insertion of the subject gene in viral vectors including recombinant retroviruses, adenovirus, adeno-associated virus, and herpes simplex virus-1, or recombinant bacterial or eukaryotic plasmids. Viral vectors can be used to transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid encoding one of the subject proteins into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding an hUBC9-proteins rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has also been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al. (1989) *PNAS* 86:9079–9083; Julan et al. (1992) *J. Gen Virol* 73:3251–3255; and Goud et al. (1983) *Virology* 163:251–254); or coupling cell surface ligands to the viral env proteins (Neda et al. (1991) *J. Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector into an amphotropic vector.

Moreover, use of retroviral gene delivery can be further enhanced by the use of tissue- or cell-specific transcriptional regulatory sequences which control expression of the UBC9-gene of the retroviral vector.

Another viral gene delivery system useful in the present invention utilitizes adenovirus-derived vectors. The genome of an adenovirus can be manipulated such that it encodes a gene product of interest, but is inactivated in terms of its ability to replicate in a normal lytic viral life cycle (see, for example, Berkner et al. (1988) *BioTechniques* 6:616; Rosenfeld et al. (1991) *Science* 252:43 1434; and Rosenfeld et al. (1992) *Cell* 68:143–155). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109–127). Expression of the inserted UBC9-gene can be under control of, for example, the E1A promoter, the major late promoter (MLP) and associated leader sequences, the E3 promoter, or exogenously added promoter sequences.

Yet another viral vector system useful for delivery of, for example, the subject hUBC9-gene, is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

Other viral vector systems that may have application in gene therapy have been derived from herpes virus, vaccinia virus, and several RNA viruses. In particular, herpes virus vectors may provide a unique strategy for persistence of the recombinant hUBC9-gene in cells of the central nervous system and ocular tissue (Pepose et al. (1994) *Invest Ophthalmol Vis Sci* 35:2662–2666).

In addition to viral transfer methods, such as those illustrated above, non-viral methods can also be employed to cause expression of a UBC9-protein, or a UBC9 antisense molecule, in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject UBC9-gene by the targeted cell. Exemplary gene delivery systems of this type include liposomal derived systems, poly-lysine conjugates, and artificial viral envelopes.

In a representative embodiment, a gene encoding one of the subject UBC9 proteins can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075). For example, lipofection of papilloma-virus infected epithelial cells can be carried out using liposomes tagged with monoclonal antibodies against, for example, squamous cells.

In similar fashion, the gene delivery system comprises an antibody or cell surface ligand which is cross-linked with a gene binding agent such as poly-lysine (see, for example, PCT publications WO93/04701, WO92/22635, WO92/20316, WO92/19749, and WO92/06180). For example, an hUBC9-gene construct encoding an antagonistic form of the protein, e.g. a dominant negative mutant, can be used to transfect HPV-infected squamous cells in vivo using a soluble polynucleotide carrier comprising an HPV viral coat protein conjugated to a polycation, e.g. poly-lysine (see U.S. Pat. No. 5,166,320). It will also be appreciated that effective delivery of the subject nucleic acid constructs via receptor-mediated endocytosis can be improved using agents which enhance escape of gene from the endosomal structures. For instance, whole adenovirus or fusogenic peptides of the influenza HA gene product can be used as part of the delivery system to induce efficient disruption of DNA-containing endosomes (Mulligan et al. (1993) *Science* 260–926; Wagner et al. (1992) *PNAS* 89:7934; and Christiano et al. (1993) *PNAS* 90:2122).

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction of the in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054–3057).

Moreover, the pharmaceutical preparation can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral packages, the pharmaceutical preparation can comprise one or more cells which produce the gene delivery system. In the case of the latter, methods of introducing the viral packaging cells may be provided by, for example, rechargeable or biodegradable devices. The generation of such implants is generally known in the art. See, for example, *Concise Encyclopedia of Medical & Dental Materials*, ed. by David Williams (MIT Press: Cambridge, Mass., 1990); Sabel et al. U.S. Pat. No. 4,883,666; Aebischer et al. U.S. Pat. No. 4,892,538; Aebischer et al. U.S. Pat. No. 5,106,627; Lim U.S. Pat. No. 4,391,909; Sefton U.S. Pat. No. 4,353,888; and Aebischer et al. (1991) *Biomaterials* 12:50–55).

This invention also pertains to a host cell transfected or transformed to express a recombinant form of the subject UBC9 proteins. The host cell may be any prokaryotic or eukaryotic cell. For example, an hUBC9 protein may be expressed in bacterial cells such as *E. coli*, insect cells (baculovirus), yeast, or mammalian cells. Other suitable host cells are known to those skilled in the art.

The term "recombinant protein" refers to a protein of the present invention which is produced by recombinant DNA techniques, wherein generally DNA encoding the UBC9 protein is inserted into a suitable expression vector which is in turn used to transform a host cell to produce the heterologous protein. Moreover, the phrase "derived from", with respect to a recombinant gene encoding the recombinant UBC9, is meant to include within the meaning of "recombinant protein" those proteins having an amino acid sequence of a native UBC9, e.g. hUBC9, xUBC9 or sUBC9, or an amino acid sequence similar thereto which is generated by mutations including substitutions and deletions of a naturally occurring form of the protein. Recombinant proteins preferred by the present invention, in addition to native proteins, are at least 90% homologous, more preferably 95% homologous and most preferably 97% homologous with an amino acid sequence shown in one of SEQ ID Nos: 2, 4 or 6. Polypeptides having an activity of a UBC9 protein, or which are antagositic thereto, and which are at least about 90%, more preferably at least about 95%, and most preferably at least about 98–99% homologous with a sequence shown in SEQ ID No: 2, 4 or 6 are also within the scope of the invention.

The present invention further pertains to recombinant UBC9 homologs which are encoded by genes derived from other non-human mammals, e.g. mouse, rat, rabbit, or pig, and which have amino acid sequences evolutionarily related to an hUBC9 protein. As described above, such recombinant UBC9 proteins preferably are capable of functioning in one of either role of an agonist or antagonist of ubiquitin-conjugation of a protein which is a substrate of UBC9. The term "evolutionarily related to", as set out above, refers to ubiquitin-conjugating enzymes having amino acid sequences which have arisen naturally, or which are mutationally derived, for example, by combinatorial mutagenesis or scanning mutagenesis, but which proteins are homologous to the human UBC9 protein represented in SEQ ID No: 2, the Xenopus UBC9 protein represented in SEQ ID No: 4, or the yeast UBC9 protein represented in SEQ ID No: 6.

The present invention further pertains to methods of producing the subject proteins. For example, a host cell transfected with an expression vector encoding one of the subject UBC9 proteins can be cultured under appropriate conditions to allow expression of the peptide to occur. The peptide may be secreted (e.g. through use of recombinantly added signal sequence) and isolated from a mixture of cells and medium containing the secreted protein. Alternatively, the peptide may be retained cytoplasmically, as it presumably is its naturally occurring form, and the cells harvested, lysed and the protein isolated. A cell culture includes host cells, media and other byproducts. Suitable media for cell culture are well known in the art. The subject UBC9 polypeptides can be isolated from cell culture medium, host cells, or both using techniques known in the art for purifying proteins including ion-exchange chromatography, gel filtration chromatography, ultrafiltration, electrophoresis, and immunoaffinity purification with antibodies raised against the protein. In a preferred embodiment, the UBC9 protein is a fusion protein containing a domain which facilitates its purification, such as the UBC9-GST fusion protein described below.

Thus, a nucleotide sequence derived from the cloning of a UBC9 protein of the present invention, encoding all or a selected portion of the protein, can be used to produce a recombinant form of the enzyme via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. p53, cyclins, phosphatases and kinases. Similar procedures, or modifications thereof, can be employed to prepare recombinant proteins, or portions thereof, by microbial means or tissue-culture technology in accord with the subject invention.

The recombinant protein can be produced by ligating the cloned gene, or a portion thereof, into a vector suitable for expression in either prokaryotic cells, eukaryotic cells, or both. Expression vehicles for production of recombinant UBC9s include plasmids and other vectors. For instance, suitable vectors for the expression of the subject proteins include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in

*Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning: A Laboratory Manual*, 2nd Ed., ed. by Sambrook, Fritsch and Maniatis (Cold Spring Harbor Laboratory Press: 1989) Chapters 16 and 17.

In some instances, it may be desirable to express the recombinant UBC9 by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When expression of a portion of the ubiquitin-conjugating enzyme is desired, i.e. a truncation mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing UBC9-derived polypeptides in a host which produces MAP (e.g., *E. coli* or CM89 or *S. cerevisiae*), or in vitro by use of purified MAP (e.g., procedure of Miller et al.).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of a UBC9 protein. In an exemplary embodiment, the VP6 capsid protein of rotavirus can be used as an immunologic carrier protein for portions of the UBC9 polypeptide, either in the monomeric form or in the form of a viral particle. The nucleic acid sequences corresponding to the portion of the UBC9 protein to which antibodies are to be raised can be incorporated into a fusion gene construct which includes coding sequences for a late vaccinia virus structural protein to produce a set of recombinant viruses expressing fusion proteins comprising a portion of the UBC9 protein as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a UBC9 protein and the poliovirus capsid protein can be created to enhance immunogenicity of the set of polypeptide antigens (see, for example, EP Publication No. 0259149; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can also be utilized, wherein a desired portion of a UBC9 protein is obtained directly from organochemical synthesis of the peptide onto an oligomeric branching lysine core (see, for example, Posnett et al. (1988) *J Biol Chem* 263:1719 and Nardelli et al. (1992) J. Immunol. 148:914). Antigenic determinants of the UBC9 proteins can also be expressed and presented by bacterial cells.

In addition to utilizing fusion proteins to enhance immunogenicity, it is widely appreciated that fusion proteins can also facilitate the expression of proteins, such as the UBC9 proteins of the present invention. For example, a UBC9 protein can be generated as a glutathione-S-transferase (GST) fusion protein. Such GST fusion proteins can enable purification of the UBC9 protein, as, for example, using glutathione-derivatized matrices (see, for example, *Current Protocols in Molecular Biology*, eds. Ausubel et al. (N.Y.: John Wiley & Sons, 1991); Smith et al. (1988) *Gene* 67:31; and Kaelin et al. (1992) *Cell* 70:351). In another embodiment, a fusion gene coding for a purification leader sequence such as a poly-(His)/enterokinase cleavage site sequence at the N-termiinus of the desired portion of the UBC9 protein, can allow purification of the expressed UBC9-fusion protein by affinity chromatography using a $Ni^{2+}$ metal resin. The purification leader sequence can then be subsequently removed by treatment with enterokinase (e.g., see Hochuli et al. (1987) *J. Chromatography* 411:177; and Janknecht et al. *PNAS* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Another aspect of the invention pertains to isolated UBC9 polypeptides, which polypeptides are isolated from or otherwise substantially free of other cellular proteins, especially other proteins of the ubiquitin conjugating system (i.e. other E1 or E2 enzymes, as well as E3 proteins or ubiquitin) normally associated with the ubiquitin-conjugating enzyme in the cellular milleau. The term "substantially free of other cellular proteins" (also referred to herein as "contaminating proteins") is defined as encompassing preparations of the subject UBC9 proteins comprising less than 20% (by dry weight) contaminating protein, and preferably comprising less than 5% contaminating protein. Functional forms of the subject UBC9 proteins can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins (particularly other enzymes of the ubiquitin system such as other E1 or E2 proteins, as well as other contaminating proteins). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins or chromatography reagents such as denaturing agents and polymers, e.g. acrylamide or agarose) substances or solutions.

Moreover, isolated peptidyl portions of the subject UBC9 proteins can also be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, one of the subject UBC9 proteins may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of, for example, ubiquitin conjugation, such as by microinjection assays or in vitro assays. In an illustrative embodiment, peptidyl portions of hUBC9 can tested for E3-binding activity, as well as inhibitory ability, by expression as, for example, thioredoxin fusion proteins each of which contains a discrete fragment of the hUBC9 protein (see, for example, U.S. Pat. Nos. 5,270,181 and 5,292,646; and PCT publication WO94/02502).

Furthermore, it is also possible to modify the structure of a UBC9 polypeptide for such purposes as enhancing therapeutic or prophylactic efficacy, or stability (e.g., shelf life ex vivo and resistance to proteolytic degradation in vivo). Such modified peptides are considered functional equivalents of peptides having an activity of, or which antagonize, a UBC9 protein as defined herein. A modified polypeptide can be produced in which the amino acid sequence has been altered, such as by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic= glycine, alanine, valine, leucine, isoleucine, serine, threonine, with serine and threonine optionally be grouped separately as aliphatic-hydroxyl; (4) aromatic= phenylalanine, tyrosine, tryptophan; (5) amide=asparagine, glutamine; and (6) sulfur–containing=cysteine and methionine. (see, for example, *Biochemistry*, 2nd ed, Ed. by L. Stryer, WH Freeman and Co.:1981). Whether a change in the amino acid sequence of a peptide results in a functional UBC9 homolog can be readily determined by assessing the ability of the variant peptide to, for instance, mediate ubiquitination in a fashion similar to the wild-type UBC9. Peptides in which more than one replacement has taken place can readily be tested in the same manner.

The invention also includes a method of generating sets of combinatorial mutants of the subject UBC9 proteins, as well as truncation and fragmentation mutants, and is especially useful for identifying potential variant sequences which are functional in ubiquitinating or inhibiting ubiquitination of cellular proteins. One purpose for screening such combinatorial libraries is, for example, to isolate novel UBC9 homologs which act as antagonist of the wild-type ("authentic") UBC9 activity, e.g. an hUBC9 homolog which inhibits ubiquitination of cell-cycle regulatory proteins, or alternatively, which possess novel activities all together. Such proteins, when expressed from recombinant DNA constructs, may be used in gene therapy protocols.

Likewise, mutagenesis can give rise to UBC9 homologs which have intracellular half-lives dramatically different than the corresponding wild-type protein. For example, the altered protein can be rendered either more stable or less stable to proteolytic degradation or other cellular process which result in destruction of, or otherwise inactivation of, a naturally occurring form of the enzyme. Such UBC9 homologs (either agonist or antagonist homologs), and the genes which encode them, can be utilized to alter the envelope of recombinant UBC9 expression by modulating the half-life of the protein. For instance, a short half-life for a recombinant hUBC9 can give rise to more transient biological effects associated with that homolog and, when part of an inducible expression system, can allow tighter control of recombinant hUBC9 levels within the cell. As above, such proteins, and particularly their recombinant nucleic acid constructs, can be used in gene therapy protocols.

In one aspect of this method, the amino acid sequences for a population of UBC9 homologs or other related proteins are aligned, preferably to promote the highest homology possible. Such a population of variants can include, for example, UBC9 homologs from one or more species, or UBC9 homologs from the same species but which differ due to mutation. Amino acids which appear at each position of the aligned sequences are selected to create a degenerate set of combinatorial sequences. For instance, alignment of the hUBC9, xUBC9 and sUBC9 sequences provided in the appended sequence listing (see also FIG. 1) can be used to generate a degenerate library of UBC9 proteins. Alternatively, the UBC9 sequence can be aligned with other UBC homologs, such as any of UBC1–8, in order to generate a library based on homolog scanning mutagenesis.

In a preferred embodiment, the combinatorial UBC9 library is produced by way of a degenerate library of genes encoding a library of polypeptides which each include at least a portion of potential UBC9 sequences. A mixture of synthetic oligonucleotides can be enzymatically ligated into gene sequences such that the degenerate set of potential UBC9 sequences are expressible as individual polypeptides, or alternatively, as a set of larger fusion proteins (e.g. for phage display) containing the set of UBC9 sequences therein.

There are many ways by which the library of potential UBC9 homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential UBC9 sequences. The synthesis of degenerate oligonucleotides is well known in the art (see, for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477). Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of UBC9 homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of, for example, degenerate UBC9 sequences created by combinatorial mutagenesis techniques.

In one illustrative screening assay, the candidate hUBC9 gene products are displayed on the surface of a cell or viral particle, and the ability of particular cells or viral particles to bind other components of the ubiquitin pathway, e.g. E1 or E3 proteins, ubiquitin, or a cellular substrate, via this gene product is detected in a "panning assay". For instance, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, fluorescently labeled molecules which bind UBC9 can be used to score for potentially functional UBC9 homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and fl are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461). In an illustrative embodiment, the recombinant phage antibody system (RPAS, Pharmacia Catalog number 27-9400-01) can be easily modified for use in expressing and screening UBC9 combinatorial libraries, and the phage-displayed candidate UBC9 proteins which are capable of binding a particular target protein, such as an E1 enzyme, an E3 protein, or particular cellular protein, are selected or enriched by panning. Thus, successive rounds of reinfection of *E. coli*, and panning can be employed to greatly enrich for UBC9 homologs that retain some ability to interact with normal targets of the wild-type UBC9, and which can then be screened for further biological activities in order to differentiate agonists and antagonists.

Other forms of mutagenesis can also be utilized to generate a combinatorial library from the subject UBC9 proteins. For example, hUBC9 homologs (both agonist and antagonist forms) can be generated and isolated from a library by screening using, for example, alanine scanning mutagenesis and the like (Ruf et al. (1994) *Biochemistry* 33:1565–1572; Wang et al. (1994) *J. Biol. Chem.* 269:3095–3099; Balint et al. (1993) *Gene* 137:109–118; Grodberg et al. (1993) *Eur. J. Biochem.* 218:597–601; Nagashima et al. (1993) *J. Biol. Chem.* 268:2888–2892; Lowman et al. (1991) *Biochemistry* 30:10832–10838; and Cunningham et al. (1989) *Science* 244:1081–1085), by linker scanning mutagenesis (Gustin et al. (1993) *Virology* 193:653–660; Brown et al. (1992) *Mol. Cell Biol.* 12:2644–2652; McKnight et al. (1982) *Science* 232:316); by saturation mutagenesis (Meyers et al. (1986) *Science* 232:613); by PCR mutagenesis (Leung et al. (1989) *Method Cell Mol Biol* 1:11–19); or by random mutagenesis (Miller et al. (1992) *A Short Course in Bacterial Genetics*, CSHL Press, Cold Spring Harbor, N.Y.; and Greener et al. (1994) *Strategies in Mol Biol* 7:32–34).

An important goal of the present invention is to provide reduction of the UBC9 proteins to small functional units that can be ultimately used to generate UBC9 mimetics, e.g. peptide or non-peptide agents, which are able to disrupt binding of UBC9 with other cellular and/or viral proteins. Thus, such mutagenic techniques as described herein are particularly useful to map the determinants of the subject UBC9 proteins which participate in protein-protein interactions involved in, for example, binding of the enzyme to other proteins of the ubiquitin-conjugating system (both cellular and viral), as well as the cellular substrate protein itself (e.g. p53, myc, fos, cyclins, etc.). To illustrate, the critical residues of hUBC9 involved in molecular recognition of p53, E6 and/or E6-AP can be determined and used to generate hUBC9-derived peptidomimetics which competitively inhibit hUBC9 binding. By employing, for example, scanning mutagenesis to map the amino acid residues of hUBC9 involved in binding E6AP, peptidomimetic compounds can be generated which mimic those residues in binding to E6AP, and which therefore can inhibit binding of the hUBC9 to E6AP and interfere with the function of E6AP in regulating the cellular half-life of p53. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71). Such peptidomimetics can serve as drugs which prevent the action of hUBC9 in the destruction of, for example, p53. Furthermore, such data concerning protein-protein interactions can be used in conjunction with the molecular model of hUBC9 described below for rational design of mimetics of this interaction. In like manner, peptidomimetics of sUBC9 can be derived which may be useful in, for example, the generation of anti-mycotic agents.

Another aspect of the invention pertains to an antibody specifically reactive with the subject UBC9 proteins. For example, by using immunogens derived from a UBC9 protein of the present invention, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide (e.g., the whole protein or an antigenic fragment which is capable of eliciting an antibody response). Techniques for conferring immunogenicity on a protein or peptide include conjugation to carriers or other techniques well known in the art. An immunogenic portion of the subject UBC9 protein can be administered in the presence of adjuvant. The progress of immunization can be monitored by detection of antibody titers in plasma or serum. Standard ELISA or other immunoassays can be used with the immunogen as an antigen to assess the levels of antibodies. In a preferred embodiment, the subject antibodies are immunospecific for an hUBC9 antigenic determinants, e.g. antigenic determinants of a protein represented by SEQ ID No: 2 or a closely related human or non-human mammalian homolog (e.g. 90 percent homologous to SEQ ID No: 2, preferably at least 95 percent homologous and more preferably at least 97 percent homologous to SEQ ID No:2). In yet a further preferred embodiment of the present invention, the anti-hUBC9 antibodies does not substantially cross react with a protein which is: e.g. less than 90 percent homologous with SEQ ID No: 2; e.g. less than 95 percent homologous with SEQ ID No: 2; e.g. less than 98–99 percent homologous with SEQ ID No:2. By "does not substantially cross-react", it is meant that: the antibody has a binding affinity for a non-homologous E2 enzyme which is at least one order of magnitude less, more preferably at least two orders of magnitude less, and most preferably at least three orders of magnitude less than the binding affinity of that antibody for the protein of SEQ ID No: 2; e.g. the antibody does not specifically bind a protein which is non-homologous to SEQ ID No: 2. Preferred antibodies against the subject xUBC9 and sUBC9 proteins have similar criteria, e.g., antibodies specific for xUBC9 or sUBC9 but which do not specifically bind proteins which do not share high sequence homology with SEQ ID No: 4 or 6, respectively.

Following immunization, anti-UBC9 antisera can be obtained and, if desired, polyclonal anti-UBC9 antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature*, 256: 495–497), the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with the subject UBC9 protein and monoclonal antibodies isolated from a culture comprising such hybridoma cells.

The term antibody as used herein is intended to include fragments thereof which are also specifically reactive with the UBC9 proteins of the present invention. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-UBC9 portion.

Both monoclonal and polyclonal antibodies (Ab) directed against the subject ubiquitin conjugating enzymes, and antibody fragments such as Fab' and F(ab')$_2$, can be used as specialty chemicals to block the action of the enzyme and allow the study of, for example, the cell cycle or cell proliferation when the subject UBC9 is inhibited, e.g. by microinjection of anti-UBC9 antibodies.

Antibodies which specifically bind, for example, hUBC9 epitopes can also be used in immunohistochemical staining of tissue samples in order to evaluate the abundance and pattern of expression of hUBC9. Anti-hUBC9 antibodies can be used diagnostically in immuno-precipitation and immuno-blotting to detect and evaluate hUBC9 levels in tissue or bodily fluid as part of a clinical testing procedure. For instance, such measurements can be useful in predictive valuations of the onset or progression of tumors. Likewise, the ability to monitor hUBC9 levels in an individual can allow determination of the efficacy of a given treatment regimen for an individual afflicted with such a disorder. The level of hUBC9 can be measured in cells isolated from bodily fluid, such as in samples of cerebral spinal fluid or blood, or can be measured in tissue, such as produced by biopsy. Diagnostic assays using anti-hUBC9 antibodies can include, for example, immunoassays designed to aid in early diagnosis of a neoplastic or hyperplastic disorder, e.g. the presence of cancerous cells in the sample, e.g. to detect cells in which a lesion of the hUBC9 gene has occurred.

Another application of anti-UBC9 antibodies is in the immunological screening of cDNA libraries constructed in expression vectors, such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of UBC9 can then be detected with antibodies, as, for example, reacting nitrocellulose filters lifted from infected plates with anti-UBC9 antibodies. Phage, scored by this assay, can then be isolated from the infected plate. Thus, the presence of hUBC9 homologs can be detected and cloned from other human sources, i.e. to identified other closely homologous human isoforms, as well as to identify UBC9 homologs in other mammals.

Moreover, the nucleotide sequence determined from the cloning of subject hUBC9 from a human cell line will further allow for the generation of probes designed for use in identifying hUBC9 homologs in other human cell-types, particularly cancer or other transformed or immortalized cells, as well as UBC9 homologs from other non-human mammals. Probes based on the yeast UBC9 sequences, sUBC9, can be generated and used to identify and phenotype mycotic infections.

In addition, nucleotide probes can be generated from the cloned sequence of the hUBC9 protein, which allow for histological screening of intact tissue and tissue samples for the presence of hUBC9 mRNA. Similar to the diagnostic uses of anti-hUBC9 antibodies, the use of probes directed to hUBC9 mRNA, or to genomic hUBC9 sequences, can be used for both predictive and therapeutic evaluation of allelic mutations which might be manifest in, for example, neoplastic or hyperplastic disorders (e.g. unwanted cell growth). Used in conjunction with anti-hUBC9 antibody immunoassays, the nucleotide probes can help facilitate the determination of the molecular basis for a developmental disorder which may involve some abnormality associated with expression (or lack thereof) of an hUBC9 protein. For instance, variation in hUBC9 synthesis can be differentiated from a mutation in the hUBC9 coding sequence.

For example, the present method provides a method for determining if a subject is at risk for a disorder characterized by unwanted cell proliferation. In preferred embodiments, the subject method can be generally characterized as comprising: detecting, in a tissue of a subject (e.g. a human patient), the presence or absence of a genetic lesion characterized by at least one of (i) a mutation of a gene encoding hUBC9 or (ii) the mis-expression of the hUBC9 gene. To illustrate, such genetic lesions can be detected by ascertaining the existence of at least one of (i) a deletion of one or more nucleotides from the hUBC9 gene, (ii) an addition of one or more nucleotides to the hUBC9 gene, (iii) a substitution of one or more nucleotides of the hUBC9 gene, (iv) a gross chromosomal rearrangement of the hUBC9 gene, (v) a gross alteration in the level of a messenger RNA transcript of the hUBC9 gene, (vi) the presence of a non-wild type splicing pattern of a messenger RNA transcript of the hUBC9 gene, and (vii) a non-wild type level of the hUBC9 protein. In one aspect of the invention there is provided a probe/primer comprising an oligonucleotide containing a region of nucleotide sequence which is capable of hybridizing to a sense or antisense sequence of SEQ ID No: 1 or naturally occurring mutants thereof, or 5' or 3' flanking sequences or intronic sequences naturally associated with the hUBC9 gene. The probe is exposed to nucleic acid of a tissue sample; and the hybridization of the probe to the sample nucleic acid is detected. In certain embodiments, detection of the lesion comprises utilizing the probe/primer in, for example, a polymerase chain reaction (PCR) (see, e.g., U.S. Pat. Nos. 4,683,195 and 4,683,202), or, alternatively, in a ligation chain reaction (LCR) (see, e.g., Landegran et al. (1988) Science 241:1077–1080; and Nakazawa et al. (1994) PNAS 91:360–364), the later of which can be particularly useful for detecting even point mutations in the hUBC9 gene. Alternatively, or additionally, the level of hUBC9 protein can be detected in an immunoassay.

Also, the use of anti-sense techniques (e.g. microinjection of antisense molecules, or transfection with plasmids whose transcripts are anti-sense with regard to, e.g. UBC9 mRNA) can be used to investigate the role of UBC9 in the cell cycle and cell proliferation, by inhibiting endogenous UBC9 production. Such techniques can be utilized in cell culture, but can also be used in the creation of transgenic animals.

Another aspect of the present invention concerns transgenic animals, e.g. as animal models for developmental and proliferative diseases, which are comprised of cells (of that animal) which contain a transgene of the present invention and which preferably (though optionally) express the subject UBC9 in one or more cells in the animal. In preferred embodiments, the expression of the transgene is restricted to specific subsets of cells, tissues or developmental stages utilizing, for example, cis-acting sequences that control expression in the desired pattern. In the present invention, such mosiac expression of the subject UBC9 proteins can be essential for many forms of lineage analysis and can additionally provide a means to assess the effects of UBC9 mutations or overexpression that might grossly alter development in small patches of tissue within an otherwise normal embryo. Toward this end, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject receptor. For example, excision of a target sequence which interferes with the expression of the receptor can be designed to activate expression of that protein. This interference with expression of the subject protein can result from a variety of mechanisms, such as spatial separation of the UBC9 gene from the promoter element or an internal stop codon. Moreover, the transgene can be made wherein the coding sequence of the UBC9 gene is flanked by recombinase recognition sequences and is initially transfected into cells in a 3' to 5' orientation with respect to the promoter element. In such an instance, inversion of the target sequence will reorient the subject UBC9 gene by placing the 5' end of the coding sequence in an orientation with respect to the promoter element which allow for promoter driven transcriptional activation.

In an illustrative embodiment, either the cre/loxP recombinase system of bacteriophage P1 (Lakso et al. (1992) PNAS 89:6232–6236; Orban et al. (1992) PNAS 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation of expression of the recombinant UBC9 gene can be regulated via regulation of recombinase expression.

Use of the these recombinase system to regulate expression of, for example, a dominant negative UBC9 gene, such as a Cys-93→Ser mutant or an antisense gene, requires the construction of a transgenic animal containing transgenes encoding both the Cre recombinase and the subject gene. Animals containing both the Cre recombinase and the UBC9 genes can be provided through the construction of "double" transgenic animals. A convenient method for providing such animals is to mate two transgenic animals each containing a transgene, e.g., one harboring the UBC9 gene, and the other harboring the recombinase gene.

One advantage derived from initially constructing transgenic animals containing a UBC9 transgene in a recombinase-mediated expressible format derives from the likelihood that the subject UBC9 protein, whether antagonistic or agonistic, will be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues, or in a developmentally restricted pattern. Thus, the creation of a founder population in which, for example, an antagonistic UBC9 transgene is silent will allow the study of progeny from that founder in which disruption of UBC9-mediated ubiquitination in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the transgene. Operators present in prokaryotic cells have been extensively characterized in vivo and in vitro and can be readily manipulated to place them in any position upstream from or within a gene by standard techniques. Such operators comprise promoter regions and regions which specifically bind proteins such as activators and repressors. One example is the operator region of the lexA gene of *E. coli* to which the LexA polypeptide binds.

Other exemplary prokaryotic regulatory sequences and the corresponding trans-activating prokaryotic proteins are given in U.S. Pat. No. 4,833,080. Thus, as described above for the recombinase-mediated activation, silent transgenic animals can be created which harbor the subject transgene under transcriptional control of a prokaryotic sequence which is not appreciably activated by eukaryotic proteins. Breeding of this transgenic animal with another animal which is transgenic for the corresponding prokaryotic trans-activator, can permit activation of the UBC9 transgene. Moreover, expression of the conditional transgenes can be induced by gene therapy-like methods (such as described above) wherein a gene encoding the trans-activating protein, e.g. a recombinase or a prokaryotic protein, is delivered to the tissue and caused to be expressed, such as in a cell-type specific manner. By this method, the UBC9 transgene could remain silent into adulthood until "turned on" by the introduction of the trans-activator.

Additionally, inducible promoters can be employed, such as the tet operator and the metallothionein promoter which can be induced by treatment with tetracycline and zinc ions, respectively (Gossen et al. (1992) *PNAS* 89:5547–5551; and Walden et al. (1987) *Gene* 61:317–327).

Methods of making knock-out or disruption transgenic animals are also generally known. See, for example, *Manipulating the Mouse Embryo*, (Cold Spring Harbor Laboratory Press, Cold Spring Harbor, N.Y., 1986). Recombinase dependent knockouts can also be generated, e.g. by homologous recombination to insert recombinase target sequences flanking portions of an endogenous UBC9 gene, such that tissue specific and/or temporal control of inactivation of an UBC9 allele can be controlled as above.

Furthermore, the present invention, by making available purified and recombinant forms of the subject UBC9 proteins, will allow the development of assays which can be used to screen for drugs which either agonize or antagonize the function of UBC9 in vivo. For instance, in addition to agents which disrupt binding of the hUBC9 protein to other cellular (or viral) proteins, inhibitors of the enzymatic activity of the subject hUBC9 can be used to prevent transfer of ubiquitin to hUBC9 and/or inhibit any downstream transfer of ubiquitin from hUBC9 (e.g. to a cell-cycle regulatory protein or an intermediary E3 complex). In a preferred embodiment, the hUBC9 inhibitor is a mechanism based inhibitor which chemically alters the enzyme, e.g. covalently binds Cys-93 (Cys-82 in the truncated sequence of SEQ ID No:2), and which is a specific inhibitor of hUBC9, e.g. has an inhibition constant 10-fold, 100-fold, or more preferably, 1000-fold different for human E2 enzymes other than the subject hUBC9 protein. Inhibitor specificity can be improved, for example, by utilizing specificity subsites of the hUBC9 enzyme involved in interactions between hUBC9 and a substrate protein, hUBC9 and an E3 or hUBC9 and an E1, which are unique to one of those complexes relative to other human E2 enzymes.

Assays for the measurement of ubiquitination can be generated in many different forms, and include assays based on cell-free systems, e.g. purified proteins or cell lysates, as well as cell-based assays which utilize intact cells. Assays as described herein can be used in conjunction with the subject hUBC9 protein to generate a ubiquitin-conjugating system for detecting agents able to inhibit hUBC9-mediated ubiquitination of a cellular or viral regulatory proteins. Such agents can be used to, for example, in the treatment of proliferative and/or differentiative disorders, to modulate apoptosis, and in the treatment of viral infections, such by adenoviruses or papillomaviruses. Similar assay systems can be constructed for the fungal UBC9s in order to detect inhibitors which may serve as anti-fungal agents. In preferred embodiments, the assay system employed for identifying anti-fungal agents are run side-by-side with the analogous assay system derived with hUBC9. Differential screening assays can be used to exploit any difference in mechanism or specificity between mammalian UBC9s and yeast UBC9s (including other yeast E2 enzymes) in order to identify agents which display a statistically significant increase in specificity for inhibiting the yeast enzymes relative to the mammalian enzymes. Thus, lead compounds which act specifically on pathogens, such as fungus involved in mycotic infections, can be developed.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target. Accordingly, potential inhibitors of UBC9 function can be detected in a cell-free assay generated by constitution of a functional ubiquitin-protein ligase system in a cell lysate, such as generated by charging a ubiquitin-depleted reticulocyte lysate (Hersko et al. (1983) *J Biol Chem* 258:8206–6214) with, in addition to UBC9 and as needed, an E1 enzyme, an E3 enzyme (cellular or viral in origin), ubiquitin, and a substrate for UBC9-dependent ubiquitination (e.g. a "target protein"). The level of ubiquitination of the target protein can be determined by quantitating the amount of ubiquitin conjugated to the protein, and is determined in the presence and absence of a test compound. A statistically significant decrease in ubiquitination (e.g., at least about 2-fold) of the target protein in the presence of the test compound is indicative of the test compound being an inhibitor of UBC9-dependent ubiquitin conjugation, with background activity from other E2 enzymes in the lysate being controlled for by performing the same assay without exogenous UBC9. It will be understood that the "target protein" can be a cellular or viral protein, such as though regulatory proteins described herein, or it may be the E3 protein or protein complex (if any) which may be the immediate downstream target of UBC9, or it could be UBC9 itself, such as where inhibitors of E1-mediated transfer of ubiquitin to UBC9 are sought.

Ubiquitination of the target protein via an in vitro ubiquitin-conjugating system, in the presence and absence of a candidate inhibitor, can be accomplished in any vessel suitable for containing the reactants. Examples include microtitre plates, test tubes, and micro-centrifuge tubes. In certain embodiments of the present assay, the in vitro assay system is generated to lack the ability to degrade the ubiquitinated target protein, such as by addition of protease inhibitors to the lysate. In such an embodiments, a wide range of detection means can be practiced to score for the presence of a ubiquitinated protein.

In one embodiment of the present assay, the products of a non-degradative ubiquitin-conjugating system are separated by gel electrophoresis, and the level of ubiquitinated target protein assessed, using standard electrophoresis protocols, by measuring an increase in molecular weight of the target protein that corresponds to the addition of one or more ubiquitin chains. For example, one or both of the target protein and ubiquitin can be labeled with a radioisotope such as $^{35}S$, $^{14}C$, or $^3H$, and the isotopically labeled protein bands quantified by autoradiographic techniques. Standardization of the assay samples can be accomplished, for instance, by adding known quantities of labeled proteins which are not themselves subject to ubiquitination or degradation under the conditions which the assay is performed. Similarly, other means of detecting electrophoretically separated proteins can be employed to quantify the level of ubiquitination of the target protein, including immunoblot analysis using antibodies specific for either the target protein or ubiquitin, or derivatives thereof. As described below, the antibody can be replaced with another molecule able to bind one of either the target protein or ubiquitin. By way of illustration, one embodiment of the present assay comprises the use of biotinylated ubiquitin in the conjugating system. The biotin label is detected in a gel during a subsequent detection step by contacting the electrophoretic products (or a blot thereof) with a streptavidin-conjugated label, such as a streptavidin linked fluorochrome or enzyme, which can be readily detected by conventional techniques. Moreover, where a reconstituted protein mixture is used (rather than a lysate) as the conjugating system, it may be possible to simply detect the target protein and ubiquitin conjugates in the gel by standard staining protocols, including Coomassie blue and silver staining.

In another embodiment, an immunoassay or similar binding assay, is used to detect and quantify the level of ubiquitinated protein produced in the ubiquitin-conjugating system. Many different immunoassay techniques are amenable for such use and can be employed to detect and quantitate the target protein:Ub conjugates. For example, the wells of a microtitre plate (or other suitable solid phase) can be coated with an antibody which specifically binds one of either the target protein or ubiquitin. After incubation of the ubiquitin-conjugating system with and without the candidate agent, the products are contacted with the matrix bound antibody, unbound material removed by washing, and ubiquitin conjugates of the target protein specifically detected. To illustrate, if an antibody which binds the target protein can be used to sequester the protein on the matrix, then a detectable anti-ubiquitin antibody can be used to score for the presence of ubiquitinated target protein on the matrix.

However, it will be clear to those skilled in the art that the use of antibodies in these binding assays is merely illustrative of binding molecules in general, and that the antibodies are readily substituted in the assay with any suitable molecule that can specifically detect one of either the target protein or the ubiquitin. For instance, a biotin-derivative of ubiquitin can be used, and streptavidin (or avidin) employed to bind the biotinylated ubiquitin. In an illustrative embodiment, wells of a microtitre plate are coated with streptavidin and contacted with the developed ubiquitin-conjugating system under conditions wherein the biotinylated ubiquitin binds to and is sequestered in the wells. Unbound material is washed from the wells, and the level of target protein (bound to the matrix via a conjugated ubiquitin moiety) is detected in each well. Alternatively, the microtitre plate wells can be coated with an antibody (or other binding molecule) which binds and sequesters the target protein on the solid support, and detection of ubiquitinated conjugates of the matrix-bound target protein are subsequently carried out using a detectable streptavidin derivative, such as an alkaline phosphatase/streptavidin complex.

In similar fashion, epitope-tagged ubiquitin, such as myc-ub (see Ellison et al. (1991) *J Biol. Chem.* 266:21150–21157; ubiquitin which includes a 10-residue sequence encoding a protein of c-myc) can be used in conjunction with antibodies to the epitope tag. A major advantage of using such an epitope-tagged ubiquitin approach for detecting Ub:protein conjugates is the ability of an N-terminal tag sequences to inhibit ubiquitin-mediated proteolysis of the conjugated target protein.

Other ubiquitin derivatives include detectable labels which do not interfere greatly with the conjugation of ubiquitin to the target protein. Such detectable labels can include fluorescently-labeled (e.g. FITC) or enzymaticaly-labeled ubiquitin fusion proteins. These derivatives can be produced by chemical cross-linking, or, where the label is a protein, by generation of a fusion protein. Several labeled ubiquitin derivatives are commercially available.

Likewise, other binding molecules can be employed in place of the antibodies that bind the target protein. For example, the target protein can be generated as a glutathione-S-transferase (GST) fusion protein. As a practical matter, such GST fusion protein can enable easy purification of the target protein in the preparation of components of the ubiquitin-conjugating system (see, for example, *Current Protocols in Molecular Biology*, eds. Ausubel et al. (N.Y.: John Wiley & Sons, 1991); Smith et al. (1988) *Gene* 67:31; and Kaelin et al. (1992) *Cell* 70:351) Moreover, glutathione derivatized matrices (e.g. glutathione-sepharose or glutathione-coated microtitre plates) can be used to sequester free and ubiquitinated forms of the target protein from the ubiquitin-conjugating system, and the level of ubiquitin immobilized can be measured as described. Likewise, where the matrix can be generated to bind ubiquitin, and the level of sequestered GST-target protein can be detected using agents which bind to the GST moiety (such as anti-GST antibodies), or, alternatively, using agents which are enzymatically acted upon by GST to produce detectable products (e.g. 1-chloro-2,4-dinitrobenzene; Habig et al. (1974) *J Biol Chem* 249:7130). Similarly, other fusion proteins involving the target protein and an enzymatic activity are contemplated by the present method. For example, fusion proteins containing β-galactosidase or luciferase, to name but a few, can be employed as labels to determine the amount of target protein sequestered on a matrix by virtue of a conjugated ubiquitin chain.

Moreover, such enzymatic fusion proteins can be used to detect and quantitate ubiquitinated target protein in a heterogeneous assay, that is one which does not require separation of the components of the conjugating system. For example, ubiquitin conjugating lysates can be generated to have a ubiquitin-dependent protease which degrades the target protein. The enzymatic activity of the fusion protein provides a detectable signal, in the presence of substrate, for measuring the level of the target protein ubiquitination. Similarly, in a non-degradative conjugating system, ubiquitination of the target protein portion of the fusion protein can allosterically influence the enzymatic activity associated with the fusion protein and thereby provides a means for monitoring the level of ubiquitin conjugation.

As additional guidance for carrying out such assays, it is noted that ubiquitin is available from commercial sources (Bovine ubiquitin, Sigma catalog no. 6253; yeast ubiquitin, Sigma catalog no. 2129), as are various modified forms of ubiquitin, as for example, fluorescein-labeled ubiquitin (Sigma catalog no. U5504), and horseradish-peroxidase labeled ubiquitin (Sigma catalog no. U9879). Biotinylated ubiquitin can be prepared from biotin-NHS (N-hydroxy-succinimide ester) using well-known techniques (biotinylation kit; Pierce catalog no. 214206, 203188 (6 atom spacer), or 203114 (14 atom spacer)). For generating certain of the detection means as described herein, some of the following reagents can be employed: polyclonal sera to ubiquitin (Sigma catalog no. U5379); labeled antibodies to biotin (Sigma catalog nos. A4541 (peroxidase conjugated) and F6762 (FITC conjugated)); labeled avidin (Sigma catalog nos. A7294, E2636 (peroxidase conjugated) and A2050, E2761 (FITC conjugated)); streptavidin (Sigma catalog no. S3762 (FITC conjugated) and S5512 (peroxidase conjugated)); Streptavidin-coated beads (Sigma catalog no. 400996; Pierce catalog no. 20347G); Streptavidin-coated 96 well microtitre plates (Pierce catalog no. 15124); Maleic anhydride-activated polystyrene 96 well plates (Pierce catalog no. 15110); and antibodies to human p53 (PharMingen catalog Nos. 14091A and 14211A), human c-myc (PharMingen catalog Nos. 14861A and 14851A), and human cyclins (PharMingen Catalog Nos: 14531A, 14541A, 14551A, 14561A, 14821A, 14781A, and 14491A). Reticulocyte lysates suitable for use in the present assay have been previously described (see, for example, Berleth et al. (1992) *J Biol Chem* 267:16405–16411; Scheffner et al. (1990) *Cell* 63:1129–1136; Scheffner et al. (1992) *EMBO J* 11:2425–2431; and Hershko et al. (1983) *J Biol Chem* 258:8206–8214), as have been methods for isolating components of the ubiquitin conjugating system (e.g. Hershko et al., supra; and Scheffner et al. (1993) *Cell* 75:495–505, describing E1 and E6/E6-AP isolation).

Furthermore, drug screening assays can be generated which do not measure ubiquitination per se, but rather detect inhibitory agents on the basis of their ability to interfere with binding of UBC9 and any other immediate upstream or downstream component of the ubiquitin conjugation pathway. In an exemplary screening assay of the present invention, the compound of interest is contacted with a mixture generated from an isolated and purified UBC9 protein, such as hUBC9 or sUBC9, and another component of the ubiquitin conjugation pathway which binds to UBC9 (e.g. a "UBC9-associated protein"), such as an E1 or E3 protein, or other cellular substrates of UBC9. Detection and quantification of UBC9 complexes provides a means for determining the compound's efficacy at inhibiting (or potentiating) complex formation between the UBC9-associated protein and UBC9. The efficacy of the compound can be assessed by generating dose response curves from data obtained using various concentrations of the test compound. Moreover, a control assay can also be performed to provide a baseline for comparison. In the control assay, isolated and purified UBC9 is added to a composition containing the UBC9-associated protein, and the formation of UBC9-containing complexes is quantitated in the absence of the test compound.

Complex formation between the UBC9 protein and UBC9-associated protein may be detected by a variety of techniques, many of which are effectively described above. For instance, modulation in the formation of complexes can be quantitated using, for example, detectably labeled proteins (e.g. radiolabeled, fluorescently labeled, or enzymatically labeled), by immunoassay, or by chromatographic detection.

Typically, it will be desirable to immobilize either UBC9 or the UBC9-associated protein to facilitate separation of UBC9/UBC9-AP complexes from uncomplexed forms of one of the proteins, as well as to accommodate automation of the assay. In an illustrative embodiment, a fusion protein can be provided which adds a domain that permits the protein to be bound to an insoluble matrix. For example, glutathione-S-transferase/UBC9 (GST/UBC9) fusion proteins can be adsorbed onto glutathione sepharose beads (Sigma Chemical, St. Louis, Mo.) or glutathione derivatized microtitre plates, which are then combined with the UBC9-associated protein, e.g. an $^{35}$S-labeled UBC9-associated protein, and the test compound and incubated under conditions conducive to complex formation. Following incubation, the beads are washed to remove any unbound UBC9-associated protein, and the matrix bead-bound radiolabel determined directly (e.g. beads placed in scintilant), or in the supernatant after the UBC9 complexes are dissociated, e.g. when microtitre plaste is used. Alternatively, after washing away unbound protein, the complexes can be dissociated from the matrix, separated by SDS-PAGE gel, and the level of UBC9-associated protein found in the matrix-bound fraction quantitated from the gel using standard electrophoretic techniques.

Other techniques for immobilizing proteins on matrices are also available for use in the subject assay. For instance, the UBC9 protein can be immobilized utilizing conjugation of biotin and streptavidin, as described above for ubiquitin. For instance, biotinylated WT1 can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates. Alternatively, antibodies reactive with UBC9 can be derivatized to the wells of the plate, and UBC9 trapped in the wells by antibody conjugation.

In similar fashion, the subject ubiquitin conjugating enzyme can be used to generate an interaction trap assay for subsequently detecting inhibitors of UBC9 biological activity (see, for example, U.S. Pat. No: 5,283,317; PCT publication WO94/10300; Zervos et al. (1993) *Cell* 72:223–232; Madura et al. (1993) *J Biol Chem* 268:12046–12054; Bartel et al. (1993) *Biotechniques* 14:920–924; and Iwabuchi et al. (1993) *Oncogene* 8:1693–1696). In an illustrative embodiment, *Saccharomyces cerevisiae* YPB2 cells are transformed simultaneously with a plasmid encoding a GAL4db-hUBC9 fusion and with a plasmid encoding the GAL4ad domain fused to p53, myc, a cyclin, E6, E6AP or some other protein which may bind to UBC9. Moreover, the strain is transformed such that the GAL4-responsive promoter drives expression of a phenotypic marker. For example, the ability to grow in the absence of histidine can depend on the expression of the HIS3 gene if it is under control of a GAL4-responsive promoter and, therefore, indicates that a functional GAL4 activator has been reconstituted through the interaction of hUBC9 and the UBC9-associated protein. Thus, agents able to inhibit hUBC9 interaction with this proteins will result in yeast cells unable to growth in the absence of histidine. Alternatively, the phenotypic marker can be one which provides a negative selection when expressed such that agents which disrupt the hUBC9 interactions confer positive growth selection to the cells.

Another aspect of the present invention concerns three-dimensional molecular models of the subject UBC9 proteins, and their use as templates for the design of agents able to inhibit at least one biological activity of the ubiquitin conjugating enzyme. An integral step to designing inhibitors of the subject ubiquitin-conjugating enzyme involves construction of computer graphics models of the ubiquitin conjugating enzyme which can be used to design pharmacophores by rational drug design. For instance, for an inhibitor to interact optimally with the subject enzyme, it will generally be desirable that it have a shape which is at least partly complimentary to that of a particular binding site of the enzyme, as for example those portions of the human ubiquitin conjugating enzyme which are involved in recognition of ubiquitin, an E1 enzyme, an E3 protein(s) such as E6 or E6AP, or a downstream target of the pathway, such as p53, myc, fos, a cyclin, etc. Additionally, other factors, including electrostatic interactions, hydrogen bonding, hydrophobic interactions, desolvation effects, and cooperative motions of ligand and enzyme, all influence the binding effect and should be taken into account in attempts to design bioactive inhibitors.

A computer-generated molecular model of the subject enzymes can be created, for example, by mapping at least the Ca-carbon positions of the UBC9 sequence of interest mapped to UBC1 from *A. thaliana* (Brookhaven databank file 1AAK.pdb), and, by homology modeling, calculate the structure of the protein and velocities of each atom at a simulation temperature. Computer programs for performing energy minimization routines are commonly used to generate molecular models. For example, both the CHARMM (Brooks et al. (1983) *J Comput Chem* 4:187–217) and AMBER (Weiner et al (1981) *J. Comput. Chem.* 106: 765) algorithms handle all of the molecular system setup, force field calculation, and analysis (see also, Eisenfield et al. (1991) *Am J Physiol* 261:C376–386; Lybrand (1991) *J Pharm Belg* 46:49–54; Froimowitz (1990) *Biotechniques* 8:640–644; Burbam et al. (1990) *Proteins* 7:99–111; Pedersen (1985) *Environ Health Perspect* 61:185–190; and Kini et al. (1991) *J Biomol Struct Dyn* 9:475–488).

Moreover, a number of programs are presently available for virtual design of enzyme inhibitors. For instance, the increasing availability of biomacromolecule structures of potential pharmacophoric molecules that have been solved crystallographically has prompted the development of a variety of direct computational methods for molecular design, in which the steric and electronic properties of substrate binding sites are used to guide the design of potential inhibitors (Cohen et al. (1990) *J. Med. Cam.* 33: 883–894; Kuntz et al. (1982) *J. Mol. Biol* 161: 269–288; Desjarlais (1988) *J. Med. Cam.* 31: 722–729; Bartlett et al. (1989) (*Spec. Publ., Roy. Soc. Chem.*) 78: 182–196; Goodford et al. (1985) *J. Med. Cam.* 28: 849–857; Desjarlais et al. *J. Med. Cam.* 29: 2149–2153). Most algorithms of this type provide a method for finding a wide assortment of chemical structures that are complementary to the shape of a binding site of the subject enzyme. Each of a set of small molecules from a particular data-base, such as the Cambridge Crystallographic Data Bank (CCDB) (Allen et al. (1973) *J. Chem. Doc.* 13: 119), is individually docked to the binding site of the hUBC9 enzyme in a number of geometrically permissible orientations with use of a docking algorithm. In an illustrative embodiment, a set of computer algorithms called DOCK, can be used to characterize the shape of invaginations and grooves that form the active sites and recognition surfaces of the subject enzyme (Kuntz et al. (1982) *J. Mol. Biol* 161: 269–288). The program can also search a database of small molecules for templates whose shapes are complementary to particular binding sites of the enzyme (Desjarlais et al. (1988) *J Med Chem* 31: 722–729). These templates normally require modification to achieve good chemical and electrostatic interactions (Desjarlais et al. (1989) *ACS Symp Ser* 413: 60–69). However, the program has been shown to position accurately known cofactors for inhibitors based on shape constraints alone.

Other exemplary virtual drug design programs include GRID (Goodford (1985, *J Med Chem* 28:849–857); Boobbyer et al. (1989, *J Med Chem* 32:1083–1094), CLIX Lawrence et al. (1992) *Proteins* 12:31–41), GROW (Moon et al. (1991) *Proteins* 11:314–328), the multiple copy simultaneous search method (MCSS) (described by Miranker et al. (1991) *Proteins* 11: 29–34), and NEWLEAD (Tschinke et al. (1993) *J Med Chem* 36: 3863,3870).

In one embodiment of the invention, the target regulatory protein is the tumor suppresser p53, and any one of the above assays or molecular modeling protocols is used to identify inhibitors of ubiquitin-mediated destruction of p53, such as by disrupting interaction of hUBC9 with p53, or interactions between hUBC9 and other proteins of the ubiquitin system such as E6 or E6AP, or alternatively, by mechanistically inhibiting the enzymatic activity of the enzyme. Many lines of evidence point to the importance of p53 in human carcinogenesis. For instance, mutations within the p53 gene are the most frequent genetic aberration thus far associated with human cancer. Although p53 can block the progression of the cell cycle when artificially expressed at high levels, it appears to be dispensable for normal development. Thus, for mice containing homozygous deletions and humans harboring germline mutations of p53, development is normal and p53 protein is expressed at very low levels in most cell types. Emerging evidence, however, suggests that p53 is a checkpoint protein that plays an important role in sensing DNA damage or regulating cellular response to stress. Under normal conditions, p53 is an unstable protein and is present at very low levels in the cell, and the level of p53 in a cell appears to be controlled at least in part by degradation involving the ubiquitin system and, based on data presented herein, is likely to be mediated by the subject hUBC9. Treating cells with UV light or X rays dramatically reduces the rate of p53 degradation, leading to a rapid increase in its concentration in the cell and presumably inducing the transcription of genes that block passage through the restriction point. However, while normal cell lines irradiated in $G_1$ fail to enter S phase, many tumor lines do not. In fact, there is a perfect correlation between cell lines that lack this feedback control and cells that have mutations in the p53 gene. These mutations are of two sorts: recessive mutations that inactivate the gene, and dominant mutations that produce abnormal proteins. Inhibitors developed using the subject hUBC9 in a ubiquitin-conjugating assay or by rational drug design could subsequently be used therapeutically to enhance the function of the p53 checkpoint by increasing the steady state concentration of p53 in the treated cell, and may therefore may be attractive therapeutic agents in cancer treatments, by increasing the fortitude of the checkpoint in transformed cells which contain wild-type p53, or by offsetting a diminishment in p53 activity by increasing the level of (mutant) p53.

Moreover, the oncogenic activity of certain viruses, such as the simian virus 40 (SV40), the adenovirus type 5 (Ad5), and the high-risk human papilloma virus types 16 and 18 (HPV16 and HPV18), has been correlated with the virus' ability to interact with and inactivate the cellular p53 protein. In the instance of the high-risk papilloma viruses, the association of the viral oncoprotein E6 with p53 leads to the specific ubiquitination and degradation of p53. This has suggested a model in which E6 immortalizes cells by deregulating cell growth control through the elimination of the p53 tumor suppresser protein. This models accounts for the observations that p53 levels are very low in HPV-immortalized cells and that the half-life of p53 in HPV16-immortalized keratinocytes is shorter than in primary keratinocytes. Thus, the present invention can be employed in the identification of an agent that can block the ubiquitin dependent degradation of p53 as mediated by E6, and thereby block proliferation of HPV-transformed cells.

The subject human ubiquitin conjugating enzyme is likely to be involved in altering the activity of other cellular proteins, particularly proteins which seem to have short half-lives, and the present invention contemplates the use of hUBC9 inhibitors, including antagonistic forms of the hUBC9 protein, to inhibit the ubiquitination of other cellular proteins by hUBC9. For example, in another embodiment, the regulatory protein ubiquitinated by hUBC9 is the myc oncoprotein. The myc regulatory protein is activated by translocation or mutation in many B-cell lymphomas or by amplification in tumor types, such as small cell lung cancer and breast cancer. The c-myc gene is the cellular homolog of the viral oncogene v-myc, which is found in a number of avian and feline retroviruses which induce leukemia and carcinomas. Myc has been implicated in the control of normal cell proliferation by many studies. In particular, it is one of the immediate early growth response genes that are rapidly induced in quiescent cells upon mitogenic induction, suggesting that it plays some role in mediating the transition from quiescence to proliferation. However, increased levels of myc itself is not sufficient to cause proliferation. In fact, in normal cells the opposite happens and the cell undergoes apoptosis. Therefore, inhibitors identified in the present assay can be used to effectively induce apoptosis in cells which do not normally overexpress myc. For example, specific delivery of these agents to lymphocytes can be used to inhibit proliferation of B- and/or T-cells in order to induce clonal deletion and generate tolerance to particular antigens.

In tumor cells, on the other hand, elevated or deregulated expression of c-myc is so widespread as to suggest a critical role for myc gene activation in multi-stage carcinomas (Field et all. (1990) *Anticancer Res* 10:1–22; and Spencer et al. (1991) *Adv Cancer Res* 56:1–48). However, such overexpression of myc in these cells is typically believed to be accompanied by expression of other cellular proteins, such as bcl-2. Interestingly, however, almost all tumor cells tested that overexpress myc readily undergo apoptosis in the presence of cytotoxic and growth-inhibitory drugs (Cotter et al. (1990) *Anticancer Res* 10:1153–1159; and Lennon et al. (1990) *Biochem Soc Trans* 18:343–345). Therefore, inhibitors of the ubiquitin-mediated degradation of myc can be used to further deregulate the expression of myc in order to render the cells even more sensitive to a chemotherapeutic treatment, or to possibly upset the careful balance of the transformed cell and cause apoptosis to occur even in the absence of a second cytotoxic drug.

The regulation of cyclin by ubiquitination is yet another therapeutic target which may implicate UBC9 inhibitors. Cyclin degradation is a key step governing exit from mitosis and progression into the next cell-cycle. For example, the transition from metaphase to anaphase which marks the end of mitosis in induced by the degradation of cyclin by a ubiquitin-mediated pathway, which in turn leads to the inactivation of cyclin-dependent kinases (cdk) operational at that cycle-cycle stage. As cells enter interphase, cyclin degradation ceases, cyclin accumulates and, as a result of a complex series of post-translational modifications, cyclin/cdk complexes are activated as kinases which drive the cell through mitosis. Cyclin degradation is thus one of the crucial events in exiting mitosis. Indeed, cyclin mutants that retain the ability to activate the cdk complexes, but which cannot be degraded, arrest the cell-cycle in mitosis. Similar cyclin-dependence exists at other points of the cell-cycle as well. Thus, inhibitors of ubiquitin-mediated degradation of a cyclin (such as where the cyclin is chosen from cyclin A, B, C, D1, D2, D3, E or F) can be used as antiproliferative agents.

Yet a further possible substrate of the subject hUBC9 is the fos oncogene product, which can undergo ubiquitin-mediated degradation in a cell and has been implicated in neoplastic transformation as well as in mediating the action of a variety of extracellular stimuli. The control of gene expression by c-fos is believed to play a critical role in cellular proliferation and developmental responses, and alterations in the normal pattern of c-fos can lead to oncogenesis. Given the prominence of c-fos as an early response gene, apparent over-expression and prolonged lifetime of c-fos, as may be caused by an inhibitor of the ubiquitin-mediated degradation of c-fos, might sufficiently unbalance the cell-cycle and cause cell death. Alternatively, such inhibitors can be used to mimic the effects of an external stimulus on the cell, such as treatment with a cytokine.

Another regulatory protein that is short-lived due to ubiquitin-mediated degradation is for the yeast MATα2 transcriptional regulator of *S. cerevisiae*, which governs the cell identity between the haploid forms, a and α, and the a/α diploid. Mutants deficient in the degradation of MATα2 have been found to have a number of defects, including inhibition of growth (Hochstrasser et al. (1990). *Cell* 61:697–708; and Chen et al. (1993) *Cell* 74: 357–369). Thus, the inhibitors of ubiquitin-mediated degradation of MATα2 can be useful in, for example, the treatment of mycotic infections, as well as the preservation of foodstuff.

EXEMPLIFICATION

The invention now being generally described, it will be more readily understood by reference to the following examples which are included merely for purposes of illustration of certain aspects and embodiments of the present invention, and are not intended to limit the invention.

Example 1

Yeast UBC9

As described below, a novel ubiquitin-conjugating enzyme has been cloned from *Saccharomyces cerevisiae*, named "sUBC9", which is apparently involved in cell-cycle regulation. Interrupted by a single intron (see FIG. 2), the sUBC9 open reading frame encodes a protein (approx. molecular weight of 18 kd; 157 amino acids; SEQ ID Nos. 5 and 6) that shares about 35% identical amino acids with other UBC proteins, including a conserved, putative active site cysteine residue. sUBC9 can form a thiolester intermediate with ubiquitin in vitro and substitution of the conserved cysteine by a serine residue results in a complete loss of sUBC9 function in vivo (see below).

UBC enzymes function primarily in pathways of proteolysis and mediate strikingly diverse cellular functions. However, whereas most known UBC genes are dispensable for life, sUBC9 mutants which were generated by gene disruption were observed to be inviable. For instance, spores of sUBC9 disruptants are able to germinate and the cells die after a few divisions. To further explore the role of sUBC9, an sUBC9 deletion strain was constructed such that it was kept alive by sUBC9 expression from the GAL1 promoter. In the presence of glucose, sUBC9 transcription is turned off and the cells were observed to stop dividing. The majority of cells arrest as large budded cells with an increased cell volume and a single nucleus close to the neck. Flow cytometric analysis (FACS) showed that these cells had replicated their DNA. The presence of short, pre-anaphase spindles in sUBC9-depleted cells suggests that although these cells fail to go through mitosis, they execute early steps of spindle formation.

An sUBC9 temperature sensitive (ts) mutant (sUBC9-1) was also generated by introducing a mutation equivalent to that of another mutant ts ubiquitin-conjugating enzyme (Ellison et al. (1991) *J Biol Chem* 266:24116–24120). When shifted to 37° C., the sUBC9-1 mutants arrested with phenotypes similar to sUBC9-depleted cells. Using this allele, it was observed that the arrest phenotype of sUBC9-1 cells was not affected by the absence of RAD9 (Weinert et al. (1988) *Science* 241:317–322), a gene which prevents cell division of cells containing incompletely replicated DNA. Furthermore, on hydroxyurea containing plates, sUBC9-1 cells released from the sUBC9 cell cycle block were able to go through another division, indicating that the sUBC9 arrest occurs at a stage subsequent to the hydroxyurea execution point (Hartwell, (1976) *J. Molec. Biol.* 104:803–817). In the absence of noticeable metaphase markers in yeast, it is concluded that sUBC9 is required after S phase at a stage defined as G2/M (Surana, et al. (1991) *Cell* 65:145–161).

In Xenopus oocytes, exit from mitosis requires the ubiquitin-dependent degradation of mitotic (B-type) cyclins (Glotzer, et al. (1991) *Nature* 349:132–138). An sUBC9 β-galactosidase fusion protein (which complements sUBC9 mutations) localizes to the nucleus and consequently sUBC9 may act on nuclear proteins such as cyclins. Consequently, it was determined whether or not sUBC9 mediates the turnover of the (B-type) cyclins CLB5 (Epstein, et al. (1992) *Genes Dev.* 6:1695–1706; Schwob, et al. (1993) *Genes Dev.* 7:1160–1175) and CLB2 (Surana, et al. (1991) *Cell* 65:145–161; Ghiara, et al. (1991) *S. Cell* 65:163–174), which are maximally expressed at the onset of S-phase and mitosis, respectively. To measure their stability during the cell cycle, CLB5 and CLB2 proteins harboring an epitope tag were expressed from the GAL promoter in synchronized cells and protein levels were followed after promoter shut-off. The CLB5 protein was essentially short-lived throughout the cell cycle with a moderate variation of its half-life ranging from an estimated 5–10 minutes in α-factor arrested G1 cells and 15–20 minutes in cells arrested in either S- or M-phase. In sUBC9-1 mutants, however, CLB5 was significantly stabilized and its half-life increased to approximately 1 hour in M-phase. sUBC9 can apparently mediate CLB5 turnover throughout the cell cycle since stabilization was also observed in non-synchronized cells. Confirming results were obtained in direct pulse chase turnover measurements of a CLB5-β-galactosidase fusion followed by immunoprecipitation with β-galactosidase-specific antibodies. This fusion protein retains regular CLB5 activity in vivo and its short half-life was again found to be sUBC9-dependent. Stabilization of CLB5 may be detrimental for normal cell proliferation as continuous high expression of CLB5 to levels still tolerated by wild-type cells strongly interfered with proliferation of sUBC9-1 mutants. Highly expressed CLB5 had a similar toxic effect in a proteosome mutant strain (pre1-1) that is known to be compromised in the degradation of ubiquitinated proteins (Heinemeyer, et al. (1991) *EMBO J.* 10:555–562; and Seufert, et al. (1992) *EMBO J.* 11:3077–3080). Thus, it may be concluded that CLB5 turnover is mediated by the ubiquitin/proteosome pathway and involves the sUBC9 ubiquitin-conjugating enzyme.

In contrast to CLB5, stability of the M-phase cyclin, CLB2, is strikingly regulated during the cell cycle. CLB2 is essentially stable during S- and M-phase (half-life>1 hour), but extremely short-lived in pre-START G1 cells (half-life<5 minutes) (Amon, et al. (1994) *Cell* 77:1037–1050). To follow the stability of the CLB2 protein when cells arrest in G1-phase, wild-type and sUBC9-1, mutant cells that constitutively express CLB2 were treated with α-factor.

Whereas RNA levels remained high, CLB2 protein fell below detectable levels in wild-type G1 cells. This was not observed in sUBC9-1 mutants where CLB2 remained sufficiently stable to accumulate after α-factor arrest, indicating that in addition to CLB5 proteolysis, sUBC9 is also involved in CLB2 turnover in pre-START G1 cells. Failure to degrade CLB2 is expected to cause an anaphase arrest, i.e. with a long spindle (Surana, et al. (1993) *EMBO J.* 12:1969–1978). However, stabilization of CLB5 and other B-type cyclins expressed earlier in the cell cycle may contribute to the pre-anaphase arrest (e.g. short) of sUBC9 mutants. The relevant substrates may even include proteins other than known cyclins whose ubiquitin-dependent degradation is required for the metaphase to anaphase transition (Holloway, et al. (1993) *Cell* 73:1393–1402).

Cyclin-dependent kinases are thought to be the master regulators of the highly ordered events of the eukaryotic cell cycle. These events are accompanied by the ordered association of the catalytic subunit of the kinase with distinct phase-specific cyclins, suggesting that rapid dismantling of one kinase-cyclin complex may be required for another to be formed. Previous data (Glotzer, et al. (1991) *Nature* 349:132–138) indicated that this may be achieved by ubiquitin-dependent degradation of certain B-type cyclins. The data presented herein indicates that both S- and M-phase B-type cyclins are destroyed by a common proteolysis pathway that involves sUBC9. Further components involved in cyclin degradation are the proteosome and certain ATPases (Ghislain, et al. (1993) *Nature* 366, 358–362) which may assist in proteosome function.

Since CLB2 is highly stable in S- or M-phase when CLB5 is rapidly turned over, CLB2 proteolysis must be regulated at a level distinct from sUBC9 action and subsequent steps in the ubiquitin pathway. Possible mechanisms are regulated stage-specific cyclin modification or recognition. Recognition by the destruction machinery may involve specific proteolytic signals within the cyclin molecule such as the "destruction box" found in all B-type cyclins (Glotzer, et al. (1991) *Nature* 349:132–138) (including CLB5 and CLB2) and specific recognition proteins called ubiquitin-ligases (Hershko, et al. (1994) *E. J. Biol. Che* 1 269:4940–4946). Recent studies (Chen, et al. (1993) *Cell* 74:357–369) indicate that some proteins bear several proteolytic signals which target the protein for degradation by distinct ubiquitination pathways. The residual instability of the cyclins (e.g. CLB5) in sUBC9 mutant cells may suggest that cyclins are also degraded by more than one degradation pathway. One might expect that cell cycle specificity of cyclin degradation is conferred by distinct proteolytic signals and/or specific components of the ubiquitin-protein ligase system.

Methods

Standard genetic and molecular biology techniques were used (e.g. see Ausubel, et al. (eds) *Current Protocols in Molecular Biology* (Green and Wiley, N.Y., 1994). sUBC9 was cloned from a yeast genomic λEMBL3A library with a PCR-generated fragment amplified with degenerate oligonucleotide primers CGGAATTCGTITA(C/T)GAAGGGIGGIGTITT and GCTCTAGAATIGTA(A/G)IGCIGGI(G/C)(T/A)CCA (I, inosine) corresponding to amino acid sequences VYEGGVF and WSPALTI (single letter code) conserved in many UBC proteins.

sUBC9 cDNA was cloned by PCR with gene-specific primers from reverse-transcribed RNA. sUBC9 was fused to β-galactosidase by inserting a 1.1 kb XbaI-ScaI fragment into YEp357R. Cells expressing this fusion, or β-galactosidase from plasmid pUB23 (Seufert, et al. (1992) *EMBO J.* 11:3077–3080) were fixed and immunostained with a mouse monoclonal antibody to β-gal (Promega).

sUBC9 depleted phenotype

Yeast strains used in this study are derivatives of DF5 (Seufert, et al. (1990) *EMBO J.* 9:45354541). A DNA fragment with the TRP1 marker inserted into sUBC9 (NcoI site at codon 36) was used for one-step gene disruption. Viability of this strain (YW077, MATα) was rescued by a GAL1 promoter-sUBC9 fusion gene (0.5 kb BamHI cDNA fragment of sUBC9 in YIpG2) integrated at the LEU2 locus. Due to considerable overexpression of the stable sUBC9 protein in YPgal medium, cells went through about 8 divisions after repressing sUBC9 synthesis in YPD. Cells were harvested, fixed in 70% ethanol and stained with DAPI for microscopy or processed for flow cytometry. A mouse monoclonal antibody to β-tubulin (Amersham) was used for in situ immunofluorescence.

sUBC9 synthesis was turned off in a strain carrying the gene under the control of the GAL1 promoter. Based on micrographs of cell morphologies (Nomarski), stained nuclei (DAPI), and DNA content determined by flow cytometry (FACS) of wild-type (WT) and cells depleted from sUBC9, the percentages of unbudded, small or large budded cells were, respectively, 48%, 35% or 17% for wild-type and 12%, 6% or 82% for sUBC9-depleted cells. The 2N DNA peak amounted to 46% (WT) or 84% (sUBC9). Analysis of phase contrast micrographs (phase) of sUBC9-depleted cells, particularly nuclei (DAPI) and spindles immunostained with tubulin antibodies (anti-tubulin), indicated that the fractions of cells with either no visible, a short or long intranuclear spindle were, respectively, 66%, 19% or 15% (n=340) for isogenic wild-type and 16%, 78% or 6% (n=280) for sUBC9-depleted cells.

CLB5 degradation assays

In order to determine CLB5 stability during the cell cycle, epitope-tagged CLB5 was expressed from the GAL1 promoter in wild-type cells synchronized by α-factor (G1), hydroxyurea (S), or nocodazole (M) and protein levels were followed on Western blots after promoter shut-off.

Briefly, CLB5 on a 2.2 kb HindIII fragment was fused to the GAL1 promoter in vector YCplac33. A triple HA1 epitope (Tyers, et al. (1992) EMBO J. 11:1773–1784) was inserted between BfrI and SpeI sites at the CLB5 carboxy terminus. The CLB5-β-gal fusion is a 2.1 kb Asp718-NsiI fragment of pGAL-CLB5 in YEp357. The temperature sensitive sUBC9-1 allele was constructed by introducing a mutation corresponding to the cdc34-1 allele (Jentsch, et al. (1992) *A. Rev. Genet.* 26:177–205) Codon 69 CCT-(Pro) of sUBC9 was changed to TCT(Ser) using PCR-mediated in vitro mutagenesis. In strain YWO102 (MATα, sUBC9-al::TRP1, LEU2::sUBC9-1) sUBC9-coding sequences (ClaI-ScaI) are replaced by the TRP1 marker and a 1.5 kb XbaI-SspI fragment expressing the sUBC9-1 allele is integrated at the LEU2 locus. The wild-type strain was YWO85 (MATα, bar1::HIS3). For cell cycle arrest, wild-type cells were treated for 3 hours at 30° C. with 50 ng/ml (α-factor, 0.1 M hydroxyurea or 15 ug/ml nocodazole; sUBC9-1 mutant cells were synchronized by nocodazole treatment at 25° C. prior to up-shift to 35° C. Arrest was confirmed by microscopic inspection and FACS analysis. Since high levels of CLB5 interfere with G1-arrest by α-factor, the regular induction (2% galactose for 12 hours) was reduced to 90 min for the experiments utilizing synchronization with α-factor. The resulting low level of CLB5 accounts for the comparably strong crossreacting signal. Time courses were started by addition of glucose to 2% final. Antibody 12CA5 and an ECL system (Amersham) were used for immunoblot analysis as previously described (Tyers, et al. (1992) *EMBO J*. 11: 1773–1784). Protein levels were quantified from suitable exposures with a laser densitometer.

Overexpression of CLB5 was found to be toxic to sUBC9-1 or proteosome mutants. Wild-type (sUBC9, PRE1) and mutant strains (sUBC9-1, pre1-1, Seufert, et al. (1992) *EMBO J*. 11:3077–3080) carrying a GAL1 promoter-CLB5 fusion gene (pGAL1-CLB5) were spotted in serial dilutions on solid media with carbon sources repressing (glucose) or inducing (galactose) CLB5 overexpression. Plates were incubated for 3 (glucose) or 5 (galactose) days at 28° C.

CLB2 degradation involves sUBC9

In order to determine CLB2 stability during the cell cycle, epitope-tagged CLB2 was expressed from the GAL10 promoter in wild-type cells arrested in G1, S, and M-phase (as above) and protein levels were followed by Western analysis after promoter shut-off. Briefly, the triple HA1 epitope sequence (Tyers, et al., supra) was added 3' to the CLB2 coding sequence. Tagged CLB2 on a 2.2 kb EcoRI-BamHI fragment was fused to the GAL10 promoter in vector YCplac33. CLB2 induction, cell cycle arrest and turnover analysis were done as described above. Levels of tagged CLB2 were followed in wild-type strain YWO85 and sUBC9 mutant strain YWO103 (MATα, bar1::HIS3, sUBC9-1::TRP1, LEU2::sUBC9-1) during treatment with α-factor at 30° C. Constitutive CLB2 expression was conferred by a 620 bp CLB2 promoter fragment extending to the XhoI site. Differences in the relative intensities of CLB5 or CLB2 to the crossreacting protein reflect differences in the their expression levels.

Example 2
Xenopus UBC9

A Xenopus homolog of UBC9 was identified by polymerase chain reaction (PCR) using degenerate primers based on the *S. cerevisiae* UBC9 described in Example 1. The nucleotide and amino acid sequence of xUBC9 are given in SEQ ID Nos. 3 and 4, respectively. The 5' primer was derived from amino acids 14–24 of the sUBC9 (KKWRKDHPFGF) and the 3' primer was based on amino acids 144–153 (YDKKVLLQAK). The primer sequences were as follows (I indicates inosine, degenerate positions are indicated by parentheses): 5' primer: CCCTCTAGAGGATCCAA(A/G)AA(A/G)TGGAG(A/G)AA(A/G)GAICA(C/T)CCITT(C/T)GGITT; 3' primer: GGGAAGCTTGAATTCTTIGC(C/T)TGIAG(C/T)AAIAC(C/T)TT(T/C)TTITC(G/A)TA. PCR reactions contained primer, 2 mM MgCl$_2$, 50 mM KCl, 10 mM Tris pH 8.3, 1.25 U Taq polymerase (Cetus), 200 uM of each deoxyribonucleoside triphosphate, and oligo dT-primed cDNA derived from total Xenopus laevis egg RNA. The PCR cycle began with a 5 minute step at 97° C. followed by 35 cycles of 1 minute at 94° C., 1 minute at 37° C., and 1 minute at 72° C. The reaction yielded a product of approximately 440 base pairs, which was cloned into the pBluescript Vector SK+ using the pCR-Script cloning system (Stratagene). The cloned PCR fragment was then used to screen a Xenopus laevis ovary λ gt10 library. DNA from positive plaques was isolated, digested with EcoRI, and cloned into S K+. Both strands were sequenced using an automated DNA sequencing system. This clone was introduced behind a GAL promoter on a single copy plasmid and tested for its ability to complement a strain which carries a temperature sensitive mutation in UBC9 (see Example 1). Complementation was observed in the presence of galactose but not glucose at 37° C. in a strain carrying Xenopus UBC9 ("xUBC9") on this plasmid. Mutation of the putative active site cysteine and a neighboring leucine (cys-93, leu-97) to serine abolished complementation activity.

A peptide derived from the C-terminal 14 amino acids of xUBC9 was used to generate polyclonal rabbit antisera. This antiserum recognized a predominant band of 18 kD in crude Xenopus extracts that comigrated with bacterially expressed xUBC9 in immunoblot experiments; this reactivity could be blocked by preincubation of the serum with an excess of xUBC9 C-terminal peptide. Antibodies were purified by affinity chromatography using xUBC9 C-terminal peptide affinity beads (Sulfolink, Pierce Chemical Co.). Crude antiserum (6 ml) was diluted 1:1 with 10 mM Tris pH 7.4 and incubated with 2 ml of xUBC9 peptide matrix for 4 hours at 4° C. Beads were washed with 10 volumes of Tris pH 7.4 followed by 10 volumes of the same buffer containing 500 mM NaCl. Antibodies were eluted with 100 mM glycine pH 2.5, and the eluate neutralized by addition of 1/10 volume 1M Tris pH 8.0. Antibodies were concentrated to 2 mg/mL, gel filtered into phosphate buffered saline, and stored at 4° C. for immunodepletion, 50 ul of purified xUBC9 antibody or 50 ul of crude non-specific rabbit antiserum was incubated with 20 ul Protein A-Sepharose beads for 90 minutes with frequent mixing at 4° C. Beads were then washed 5 times with buffer Q-A.

Example 3
Human UBC9

A human homolog of the UBC9 gene ('hUBC9") was generated using the polymerase chain reaction (PCR) and degenerate oligonucleotide primers based on the DNA sequences of the Xenopus UBC9 sequence. The top strand or upstream primer was derived from amino acids 12 to 24 of xUBC9 (ERKAWRKDHPFGF). The bottom strand or downstream primer was derived from amino acids 143 to 153 of xUBC9 (EYEKRVRAQAK). The DNA sequences for the degenerate primers are as follows (where "I" indicates inosine and degenerate positions are in parentheses): upstream primer, 5'-CCTGAGGATCCGAATTCGA(A/G)(C/A)GIAA(A/G)GCITGG(C/A)GIAA(A/G)GA(TIC)CA(T/C)CCITT(T/C)GG ITT-3'; downstream primer, 5'-GAGCTTCTAGAAAGCTT(T/C)TTIGC(T/C)TGIGCIC(G/T)IACIC(G/T)(T/C)TT(T/C)TC(A/G)TA(T/G)TC-3'. Total HeLa cell RNA (10 μg) was used to generate cDNA using 300 ng random primers per 35 μl reaction. The PCR reaction contained 5 μg of each of the two degenerate oligonucleotides, 10 mM Tris-HCl pH 8.3, 1.5 mM MgCl$_2$, 50 mM KCl, 0.3 mM of each deoxyribonucleoside triphosphate, 3.0 μl cDNA from total HeLa cell RNA, and 5 units of Taq polymerase per 100 μl reaction. The PCR reaction was incubated at 95° C. for 1 minute, 56° C. for 1 minute, and 72° C. for 1 minute for a total of 35 cycles, followed by one 10 minute cycle at 72° C. The PCR product generated was approximately 450 bp and was restricted with EcoRI and XbaI, gel isolated, and then cloned into pBluescript SK+. The resulting plasmid was sequenced using the T3 and T7 primers. The nucleotide and amino acid sequence of hUBC9 are given in SEQ ID Nos. 1 and 2, respectively.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A substantially pure nucleic acid comprising a nucleotide sequence encoding a human ubiquitin conjugating enzyme (UBC) having the amino acid sequence of SEQ ID No: 2.

2. The nucleic acid of claim 1, wherein said UBC-encoding nucleotide sequence hybridizes to a nucleic acid probe corresponding to at least 12 consecutive nucleotides of SEQ ID No. 1 upon hybridization in 6.0×sodium chloride/sodium citrate (SSC) at 45° C., followed by washing in 0.2×SSC at 50° C.

3. The nucleic acid of claim 1, further comprising a transcriptional regulatory sequence operably linked to said nucleotide sequence so as to render said nucleotide sequence suitable for use as an expression vector.

4. An expression vector, capable of replicating in at least one of a prokaryotic cell and eukaryotic cell, comprising the nucleic acid of claim 1.

5. A host cell transfected with the expression vector of claim 4.

6. A method of producing a recombinant ubiquitin conjugating enzyme comprising culturing the cell of claim 5 in a cell culture medium to express said ubiquitin conjugating enzyme and isolating said ubiquitin conjugating enzyme from said cell culture.

7. A recombinant polynucleotide comprising a nucleotide sequence encoding a human ubiquitin conjugating enzyme (UBC) having the amino acid sequence of SEQ ID No. 2, said nucleotide sequence operably linked to a transcriptional regulatory sequence in an open reading frame and translatable to a polypeptide capable of functioning in either the role of an agonist of cell cycle regulation or an antagonist of cell cycle regulation.

8. The nucleic acid of claim 1 wherein the nucleotide sequence corresponds to SEQ ID No 1.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 428 base pairs
      (B) TYPE: nucleic acid
      (C) STRANDEDNESS: both
      (D) TOPOLOGY: linear (ii) MOLECULE TYPE: cDNA (ix) FEATURE:
      (A) NAME/KEY: CDS
      (B) LOCATION: 1..426

(xi) SEQUENCE DESCRIPTION: SEQ ID NO:1:

```
GAG AGG AAA GCG TGG CGA AAG GAT CAT CCG TTC GGG TTC GTG GCT GTC      48
Glu Arg Lys Ala Trp Arg Lys Asp His Pro Phe Gly Phe Val Ala Val
 1               5                  10                  15

CCA ACA AAA AAT CCA GAT GGC ACG ATG AAC CTC ATG AAC TGG GAG TGC      96
Pro Thr Lys Asn Pro Asp Gly Thr Met Asn Leu Met Asn Trp Glu Cys
             20                  25                  30

GCC ATT CCA GGA AAG AAA GGG ACT CCG TGG GAA GGA GGC TTG TTT AAA     144
Ala Ile Pro Gly Lys Lys Gly Thr Pro Trp Glu Gly Gly Leu Phe Lys
         35                  40                  45

CTA CGG ATG CTT TTC AAA GAT GAT TAT CCA TCT TCG CCA CCA AAA TGT     192
Leu Arg Met Leu Phe Lys Asp Asp Tyr Pro Ser Ser Pro Pro Lys Cys
     50                  55                  60

AAA TTC GAA CCA CCA TTA TTT CAC CCG AAT GTG TAC CCT TCG GGG GCA     240
Lys Phe Glu Pro Pro Leu Phe His Pro Asn Val Tyr Pro Ser Gly Ala
 65                  70                  75                  80

GTG TGC CTG TCC ATC TTA GAG GAG GAC AAG GAC TGG AGG CCA GCC ATC     288
Val Cys Leu Ser Ile Leu Glu Glu Asp Lys Asp Trp Arg Pro Ala Ile
                 85                  90                  95

ACA ATC AAA CAG ATC CTA TTA GGA ATA CAG GAA CTT CTA AAT GAA CCA     336
Thr Ile Lys Gln Ile Leu Leu Gly Ile Gln Glu Leu Leu Asn Glu Pro
            100                 105                 110

AAT ATC CAA GAC CCA GCT CAA GCA GAG GCC TAC ACG ATT TAC TGC CAA     384
Asn Ile Gln Asp Pro Ala Gln Ala Glu Ala Tyr Thr Ile Tyr Cys Gln
        115                 120                 125

AAC AGA GTG GAC TAC GAA ACG TCC GCG CCC AAG CCA AGA AGC             426
Asn Arg Val Asp Tyr Glu Thr Ser Ala Pro Lys Pro Arg Ser
    130                 135                 140

TT                                                                   428
```

(2) INFORMATION FOR SEQ ID NO:2:

(i) SEQUENCE CHARACTERISTICS:
      (A) LENGTH: 142 amino acids
      (B) TYPE: amino acid
      (D) TOPOLOGY: linear (ii) MOLECULE TYPE: protein (xi) SEQUENCE DESCRIPTION: SEQ ID NO:2:

```
Glu Arg Lys Ala Trp Arg Lys Asp His Pro Phe Gly Phe Val Ala Val
 1               5                  10                  15

Pro Thr Lys Asn Pro Asp Gly Thr Met Asn Leu Met Asn Trp Glu Cys
             20                  25                  30
```

```
Ala Ile Pro Gly Lys Lys Gly Thr Pro Trp Glu Gly Gly Leu Phe Lys
         35                  40                  45

Leu Arg Met Leu Phe Lys Asp Asp Tyr Pro Ser Ser Pro Pro Lys Cys
 50                  55                  60

Lys Phe Glu Pro Pro Leu Phe His Pro Asn Val Tyr Pro Ser Gly Ala
 65                  70                  75                  80

Val Cys Leu Ser Ile Leu Glu Glu Asp Lys Asp Trp Arg Pro Ala Ile
                 85                  90                  95

Thr Ile Lys Gln Ile Leu Leu Gly Ile Gln Glu Leu Leu Asn Glu Pro
            100                 105                 110

Asn Ile Gln Asp Pro Ala Gln Ala Glu Ala Tyr Thr Ile Tyr Cys Gln
            115                 120                 125

Asn Arg Val Asp Tyr Glu Thr Ser Ala Pro Lys Pro Arg Ser
130                 135                 140

(2) INFORMATION FOR SEQ ID NO:3:

(i) SEQUENCE CHARACTERISTICS:
        (A) LENGTH: 477 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..474

(xi) SEQUENCE DESCRIPTION: SEQ ID NO:3:

ATG TCT GGC ATA GCC CTG AGC AGA CTT GCA CAG GAG AGA AAA GCT TGG         48
Met Ser Gly Ile Ala Leu Ser Arg Leu Ala Gln Glu Arg Lys Ala Trp
 1               5                  10                  15

AGA AAA GAC CAT CCT TTT GGT TTT GTG GCA GTA CCA ACG AAA AAT CCA         96
Arg Lys Asp His Pro Phe Gly Phe Val Ala Val Pro Thr Lys Asn Pro
                 20                  25                  30

GAT GGC ACA ATG AAT TTG ATG AAC TGG GAA TGT GCT ATT CCA GGC AAG        144
Asp Gly Thr Met Asn Leu Met Asn Trp Glu Cys Ala Ile Pro Gly Lys
             35                  40                  45

AAA GGG ACC CCC TGG GAA GGT GGC TTA TTT AAA TTA CGG ATG CTT TTT        192
Lys Gly Thr Pro Trp Glu Gly Gly Leu Phe Lys Leu Arg Met Leu Phe
 50                  55                  60

AAG GAT GAT TAT CCC TCG TCA CCT CCT AAA TGT AAA TTT GAG CCA CCC        240
Lys Asp Asp Tyr Pro Ser Ser Pro Pro Lys Cys Lys Phe Glu Pro Pro
 65                  70                  75                  80

CTA TTT CAT CCG AAT GTC TAT CCT TCA GGC ACA GTG TGT CTG TCT ATC        288
Leu Phe His Pro Asn Val Tyr Pro Ser Gly Thr Val Cys Leu Ser Ile
                 85                  90                  95

TTA GAA GAA GAT AAG GAT TGG AGG CCA GCA ATC ACA ATT AAA CAG ATC        336
Leu Glu Glu Asp Lys Asp Trp Arg Pro Ala Ile Thr Ile Lys Gln Ile
            100                 105                 110

TTG TTA GGA ATA CAA GAA CTT CTA AAT GAA CCA AAT ATA CAA GAT CCA        384
Leu Leu Gly Ile Gln Glu Leu Leu Asn Glu Pro Asn Ile Gln Asp Pro
            115                 120                 125

GCT CAA GCA GAG GCA TAC ACA ATT TAC TGC CAA AAC AGA GTT GAA TAT        432
Ala Gln Ala Glu Ala Tyr Thr Ile Tyr Cys Gln Asn Arg Val Glu Tyr
130                 135                 140

GAA AAA AGA GTC AGA GCA CAA GCC AAG AAG TTT GCG CCA TCA                474
Glu Lys Arg Val Arg Ala Gln Ala Lys Lys Phe Ala Pro Ser
145                 150                 155
```

TAA                                                                477

(2) INFORMATION FOR SEQ ID NO:4:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO:4:

Met Ser Gly Ile Ala Leu Ser Arg Leu Ala Gln Glu Arg Lys Ala Trp
 1               5                  10                  15

Arg Lys Asp His Pro Phe Gly Phe Val Ala Val Pro Thr Lys Asn Pro
            20                  25                  30

Asp Gly Thr Met Asn Leu Met Asn Trp Glu Cys Ala Ile Pro Gly Lys
        35                  40                  45

Lys Gly Thr Pro Trp Glu Gly Gly Leu Phe Lys Leu Arg Met Leu Phe
    50                  55                  60

Lys Asp Asp Tyr Pro Ser Ser Pro Lys Cys Lys Phe Glu Pro Pro
65                  70                  75                  80

Leu Phe His Pro Asn Val Tyr Pro Ser Gly Thr Val Cys Leu Ser Ile
                85                  90                  95

Leu Glu Glu Asp Lys Asp Trp Arg Pro Ala Ile Thr Ile Lys Gln Ile
            100                 105                 110

Leu Leu Gly Ile Gln Glu Leu Leu Asn Glu Pro Asn Ile Gln Asp Pro
        115                 120                 125

Ala Gln Ala Glu Ala Tyr Thr Ile Tyr Cys Gln Asn Arg Val Glu Tyr
    130                 135                 140

Glu Lys Arg Val Arg Ala Gln Ala Lys Lys Phe Ala Pro Ser
145                 150                 155

(2) INFORMATION FOR SEQ ID NO:5:

(i) SEQUENCE CHARACTERISTICS:
        (A) LENGTH: 471 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..471

(xi) SEQUENCE DESCRIPTION: SEQ ID NO:5:

ATG AGT AGT TTG TGT CTA CAG CGT CTT CAG GAA GAA AGG AAA AAA TGG      48
Met Ser Ser Leu Cys Leu Gln Arg Leu Gln Glu Glu Arg Lys Lys Trp
 1               5                  10                  15

AGA AAG GAT CAT CCA TTT GGA TTT TAT GCC AAA CCA GTT AAG AAA GCT      96
Arg Lys Asp His Pro Phe Gly Phe Tyr Ala Lys Pro Val Lys Lys Ala
            20                  25                  30

GAT GGG TCC ATG GAT TTA CAG AAA TGG GAA GCT GGT ATC CCA GGC AAA     144
Asp Gly Ser Met Asp Leu Gln Lys Trp Glu Ala Gly Ile Pro Gly Lys
        35                  40                  45

GAA GGT ACA AAC TGG GCG GGT GGT GTG TAC CCA ATT ACA GTC GAA TAT     192
Glu Gly Thr Asn Trp Ala Gly Gly Val Tyr Pro Ile Thr Val Glu Tyr
    50                  55                  60

CCA AAT GAA TAT CCT TCA AAA CCT CCA AAG GTT AAA TTT CCA GCC GGA     240
Pro Asn Glu Tyr Pro Ser Lys Pro Pro Lys Val Lys Phe Pro Ala Gly

```
                65                          70                          75                          80
TTT  TAT  CAT  CCA  AAC  GTG  TAT  CCA  AGT  GGC  ACA  ATA  TGT  TTA  AGT  ATT       288
Phe  Tyr  His  Pro  Asn  Val  Tyr  Pro  Ser  Gly  Thr  Ile  Cys  Leu  Ser  Ile
                    85                          90                          95

TTA  AAT  GAA  GAT  CAA  GAT  TGG  AGA  CCC  GCC  ATC  ACG  TTA  AAA  CAA  ATT       336
Leu  Asn  Glu  Asp  Gln  Asp  Trp  Arg  Pro  Ala  Ile  Thr  Leu  Lys  Gln  Ile
               100                         105                         110

GTT  CTT  GGG  GTT  CAG  GAT  CTT  TTA  GAC  TCT  CCA  AAT  CCA  AAT  TCC  CCT       384
Val  Leu  Gly  Val  Gln  Asp  Leu  Leu  Asp  Ser  Pro  Asn  Pro  Asn  Ser  Pro
               115                         120                         125

GCT  CAA  GAG  CCT  GCA  TGG  AGA  TCA  TTT  TCA  AGA  AAT  AAG  GCG  GAA  TAT       432
Ala  Gln  Glu  Pro  Ala  Trp  Arg  Ser  Phe  Ser  Arg  Asn  Lys  Ala  Glu  Tyr
               130                         135                         140

GAC  AAG  AAA  GTT  TTG  CTT  CAA  GCT  AAA  CAG  TAC  TCT  AAA                      471
Asp  Lys  Lys  Val  Leu  Leu  Gln  Ala  Lys  Gln  Tyr  Ser  Lys
145                         150                         155
```

(2) INFORMATION FOR SEQ ID NO:6:

(i) SEQUENCE CHARACTERISTICS:
        (A) LENGTH: 157 amino acids
        (B) TYPE: amino acid
        (D) TOPOLOGY: linear (ii) MOLECULE TYPE: protein (xi) SEQUENCE DESCRIPTION: SEQ ID NO:6:

```
Met  Ser  Ser  Leu  Cys  Leu  Gln  Arg  Leu  Gln  Glu  Glu  Arg  Lys  Lys  Trp
 1                  5                          10                         15

Arg  Lys  Asp  His  Pro  Phe  Gly  Phe  Tyr  Ala  Lys  Pro  Val  Lys  Lys  Ala
                    20                         25                         30

Asp  Gly  Ser  Met  Asp  Leu  Gln  Lys  Trp  Glu  Ala  Gly  Ile  Pro  Gly  Lys
               35                          40                         45

Glu  Gly  Thr  Asn  Trp  Ala  Gly  Gly  Val  Tyr  Pro  Ile  Thr  Val  Glu  Tyr
          50                          55                         60

Pro  Asn  Glu  Tyr  Pro  Ser  Lys  Pro  Pro  Lys  Val  Lys  Phe  Pro  Ala  Gly
65                       70                          75                         80

Phe  Tyr  His  Pro  Asn  Val  Tyr  Pro  Ser  Gly  Thr  Ile  Cys  Leu  Ser  Ile
                    85                         90                         95

Leu  Asn  Glu  Asp  Gln  Asp  Trp  Arg  Pro  Ala  Ile  Thr  Leu  Lys  Gln  Ile
               100                         105                        110

Val  Leu  Gly  Val  Gln  Asp  Leu  Leu  Asp  Ser  Pro  Asn  Pro  Asn  Ser  Pro
               115                         120                        125

Ala  Gln  Glu  Pro  Ala  Trp  Arg  Ser  Phe  Ser  Arg  Asn  Lys  Ala  Glu  Tyr
               130                         135                        140

Asp  Lys  Lys  Val  Leu  Leu  Gln  Ala  Lys  Gln  Tyr  Ser  Lys
145                         150                         155
```

(2) INFORMATION FOR SEQ ID NO:7:

(i) SEQUENCE CHARACTERISTICS:
        (A) LENGTH: 1492 base pairs
        (B) TYPE: nucleic acid
        (C) STRANDEDNESS: both
        (D) TOPOLOGY: linear (ii) MOLECULE TYPE: DNA (genomic)

(ix) FEATURE:
        (A) NAME/KEY: exon
        (B) LOCATION: 524..562

-continued (ix) FEATURE:
    (A) NAME/KEY: intron
    (B) LOCATION: 563..672

(ix) FEATURE:
    (A) NAME/KEY: exon
    (B) LOCATION: 673..1104

(xi) SEQUENCE DESCRIPTION: SEQ ID NO:7:

| | | | | | |
|---|---|---|---|---|---|
| TCTAGAGCAC | TAATCAGTTT | ATTAAAATCT | TCTGTCTTCA | CATTATTCTC | GTTACCGTTA | 60 |
| TTTTTCATCA | AATTTGCGAA | CTCATTTTGC | AAATCTACCA | TCATTTCTTT | CAATTCTGGG | 120 |
| TCCTCTTCAG | ATTCATTAGC | TACCTGTACG | CCATCACTGT | CCTTACTTTC | GGCATTCTTC | 180 |
| TCTTTGTTTT | CACTATCGTT | GTACACAGAA | CCCTTCGCTT | GCACATCATC | GGGCTCTGCT | 240 |
| TCATCCAGTT | TAGTGGGATC | TTCATCTAAA | AGGTCATCCA | AATCATCAAA | ATTATCGTAC | 300 |
| TCGTTTTCAT | TCATTACTTC | GTGTTGTATG | TTTGGCATTT | CTTCTTTCCG | TCAATACTTC | 360 |
| GGTTCCCACA | ATTTGTAATT | CTTTCTTCAC | TTTATATCTC | TCAGAAACCG | CGTTTAACAT | 420 |
| CTGGAAATTA | AAAATTATTC | CTGTCTCCAT | AACAAACATT | TAAAAAAAGA | AGAGAAATTT | 480 |
| AGCATAGGAT | AAGCACACAC | TGGCACCATT | TTTTGGAAGC | AATATGAGTA | GTTTGTGTCT | 540 |
| ACAGCGTCTT | CAGGAAGAAA | GGTAAGTAGT | AGTTTTCCTC | CTTTTATGCT | TACATTCTGT | 600 |
| AGGCATACAC | AATTTCATCC | AGCGGTATAC | TAACAAATCG | ATGAACTTAA | CTTGTTTTAC | 660 |
| TTGAATAACA | GAAAAAAATG | GAGAAAGGAT | CATCCATTTG | GATTTTATGC | CAAACCAGTT | 720 |
| AAGAAAGCTG | ATGGGTCCAT | GGATTTACAG | AAATGGGAAG | CTGGTATCCC | AGGCAAAGAA | 780 |
| GGTACAAACT | GGGCGGGTGG | TGTGTACCCA | ATTACAGTCG | AATATCCAAA | TGAATATCCT | 840 |
| TCAAAACCTC | CAAAGGTTAA | ATTTCCAGCC | GGATTTTATC | ATCCAAACGT | GTATCCAAGT | 900 |
| GGCACAATAT | GTTTAAGTAT | TTTAAATGAA | GATCAAGATT | GGAGACCCGC | CATCACGTTA | 960 |
| AAACAAATTG | TTCTTGGGGT | TCAGGATCTT | TTAGACTCTC | CAAATCCAAA | TTCCCCTGCT | 1020 |
| CAAGAGCCTG | CATGGAGATC | ATTTTCAAGA | AATAAGGCGG | AATATGACAA | GAAAGTTTTG | 1080 |
| CTTCAAGCTA | AACAGTACTC | TAAATAGAGG | GAATCCATCT | TTCCCATTCT | TCCTCCTTTT | 1140 |
| GTACTTTATT | TAACTAATGT | CGTTGTGTAA | CAAAAATAGA | GCAAATAAC | ATTATTTACA | 1200 |
| AATTCTCAAA | AATAATTTTT | TGCTCTTTGT | TTCTTATGCT | AAGTAAATAG | AAAGATATTT | 1260 |
| TTTGTACCAT | TTTCTATAAG | TATGGCAACT | ATATACACTT | TAATAAATCT | ATTGGTTAGT | 1320 |
| AGAATTTTCA | TTCATTTTGT | AGTGAATGAA | ACTAGCCAAC | GTAGTAAAGC | AATCATGGCA | 1380 |
| TCTTTCTTTT | AGTTCGGGAT | TTTTGTTTTT | ATCAACCATT | TTGAATTGCT | GCCTCAAATT | 1440 |
| TGGTACAACT | TGGTCTTTTA | GAATAGATAA | AAATCCACCC | CTTACAAATA | TT | 1492 |